US010695522B2

(12) United States Patent
Cariola et al.

(10) Patent No.: US 10,695,522 B2
(45) Date of Patent: Jun. 30, 2020

(54) RESPIRATORY PRESSURE THERAPY DEVICE

(71) Applicant: ResMed Pty Ltd, Bella Vista, New South Wales (AU)

(72) Inventors: Melanie Lucia Cariola, Sydney (AU); Barton John Kenyon, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 458 days.

(21) Appl. No.: 15/456,839

(22) Filed: Mar. 13, 2017

(65) Prior Publication Data
US 2017/0259019 A1    Sep. 14, 2017

Related U.S. Application Data

(60) Provisional application No. 62/307,882, filed on Mar. 14, 2016.

(51) Int. Cl.
*A61M 16/10* (2006.01)
*A61M 16/00* (2006.01)
(Continued)

(52) U.S. Cl.
CPC .... *A61M 16/1055* (2013.01); *A61M 16/0069* (2014.02); *A61M 16/026* (2017.08);
(Continued)

(58) Field of Classification Search
CPC .. A61M 2202/0208; A61M 2202/0007; A61M 16/0069; A61M 16/026;
(Continued)

(56) References Cited

U.S. PATENT DOCUMENTS 6,581,594 B1    6/2003  Drew et al.
2009/0044808 A1    2/2009  Guney et al.
(Continued)

FOREIGN PATENT DOCUMENTS

WO    1998/034665    8/1998
WO    2000/078381    12/2000
(Continued)

OTHER PUBLICATIONS

West, John B., "*Respiratory Physiology*", Lippincott Williams & Wilkins, 9th edition published 2011 (8 pages).
U.S. Appl. No. 62/307,882, filed Mar. 14, 2016.

*Primary Examiner* — Imani N Hayman
(74) *Attorney, Agent, or Firm* — Nixon & Vanderhye P.C.

(57) ABSTRACT

Apparatus for generating a supply of air at positive pressure for the amelioration or treatment of a respiratory disorder comprising a housing, a blower structured and configured to produce a flow of air at positive pressure, a flexible connector electrically and physically connected to the blower; and a blower rotation limitation structure configured to reduce rotation of the blower during use. The apparatus may comprise first and second blower suspensions for holding opposite ends of the blower. The blower suspension(s) may be flexible and in tension. The apparatus may comprise one or more connector anchors for anchoring a longitudinal middle section of the flexible connector to another part of the apparatus.

37 Claims, 33 Drawing Sheets

(51) Int. Cl.
*A61M 16/16* (2006.01)
*A61M 16/06* (2006.01)

(52) U.S. Cl.
CPC ....... *A61M 16/0633* (2014.02); *A61M 16/109* (2014.02); *A61M 16/16* (2013.01); *A61M 16/161* (2014.02); *A61M 16/162* (2013.01); *A61M 2016/0027* (2013.01); *A61M 2016/0036* (2013.01); *A61M 2202/0208* (2013.01); *A61M 2205/3368* (2013.01); *A61M 2205/3389* (2013.01); *A61M 2205/42* (2013.01); *A61M 2205/502* (2013.01); *A61M 2205/52* (2013.01); *A61M 2205/8206* (2013.01); *A61M 2209/086* (2013.01)

(58) Field of Classification Search
CPC .......... A61M 16/0633; A61M 16/1055; A61M 16/109; A61M 16/16; A61M 16/161; A61M 16/162; A61M 2016/0027; A61M 2016/0036; A61M 2205/3368; A61M 2205/3389; A61M 2205/42; A61M 2205/502; A61M 2205/52; A61M 2205/8206; A61M 2209/086; C12Q 1/6886; C12Q 2600/118; C12Q 2600/156; G16B 99/00

See application file for complete search history.

(56) References Cited

U.S. PATENT DOCUMENTS

| | | | |
|---|---|---|---|
| 2009/0050156 A1 | 2/2009 | Ng et al. | |
| 2013/0306072 A1* | 11/2013 | Moir | A61M 16/0066 128/204.18 |
| 2014/0158131 A1* | 6/2014 | Kenyon | A61M 16/0066 128/204.18 |
| 2015/0136127 A1* | 5/2015 | Dimatteo | A61M 16/0816 128/202.27 |

FOREIGN PATENT DOCUMENTS

| | | |
|---|---|---|
| WO | 2011/023874 | 3/2011 |
| WO | 2012/171072 | 12/2012 |
| WO | 2013/020167 | 2/2013 |

\* cited by examiner

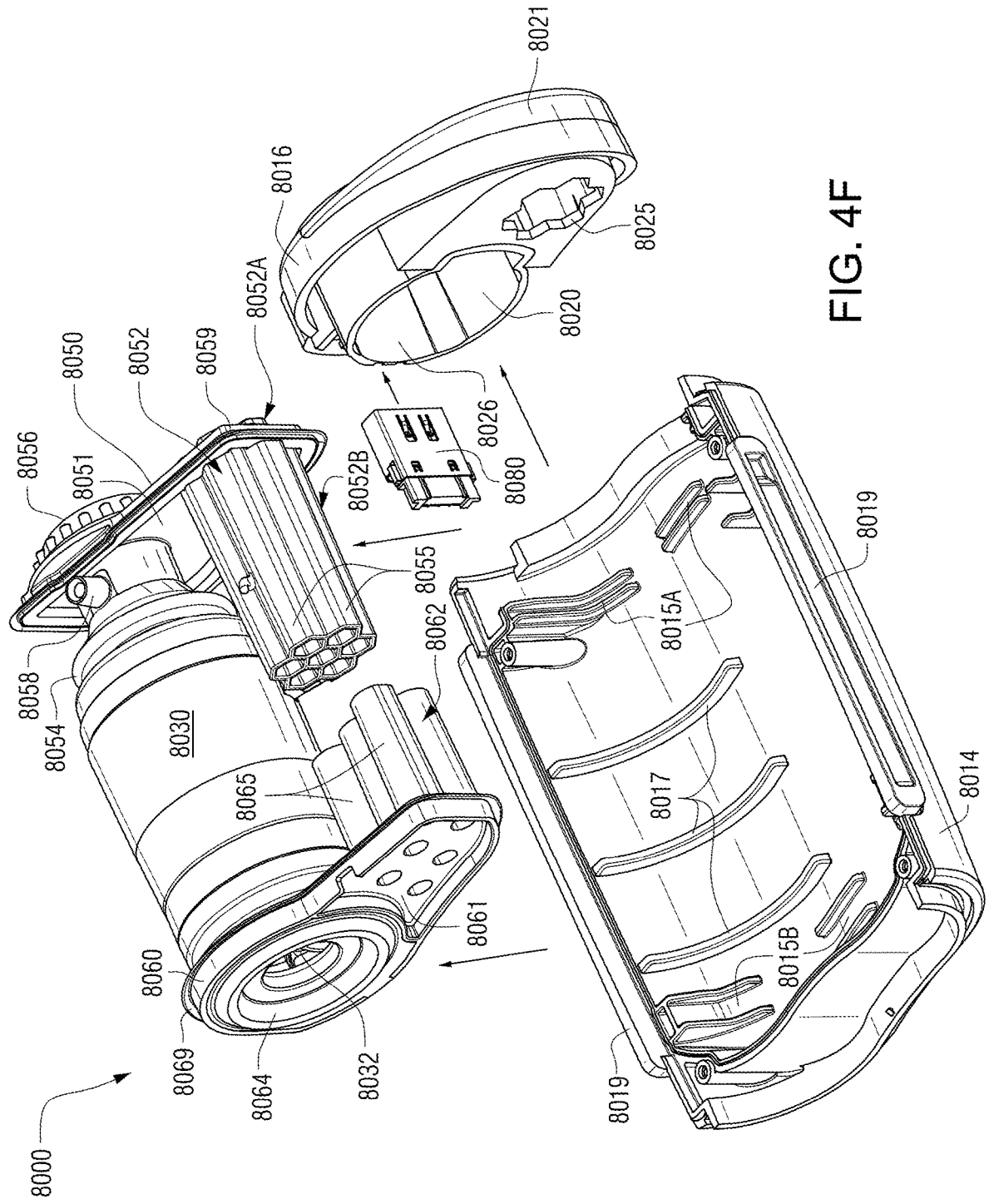

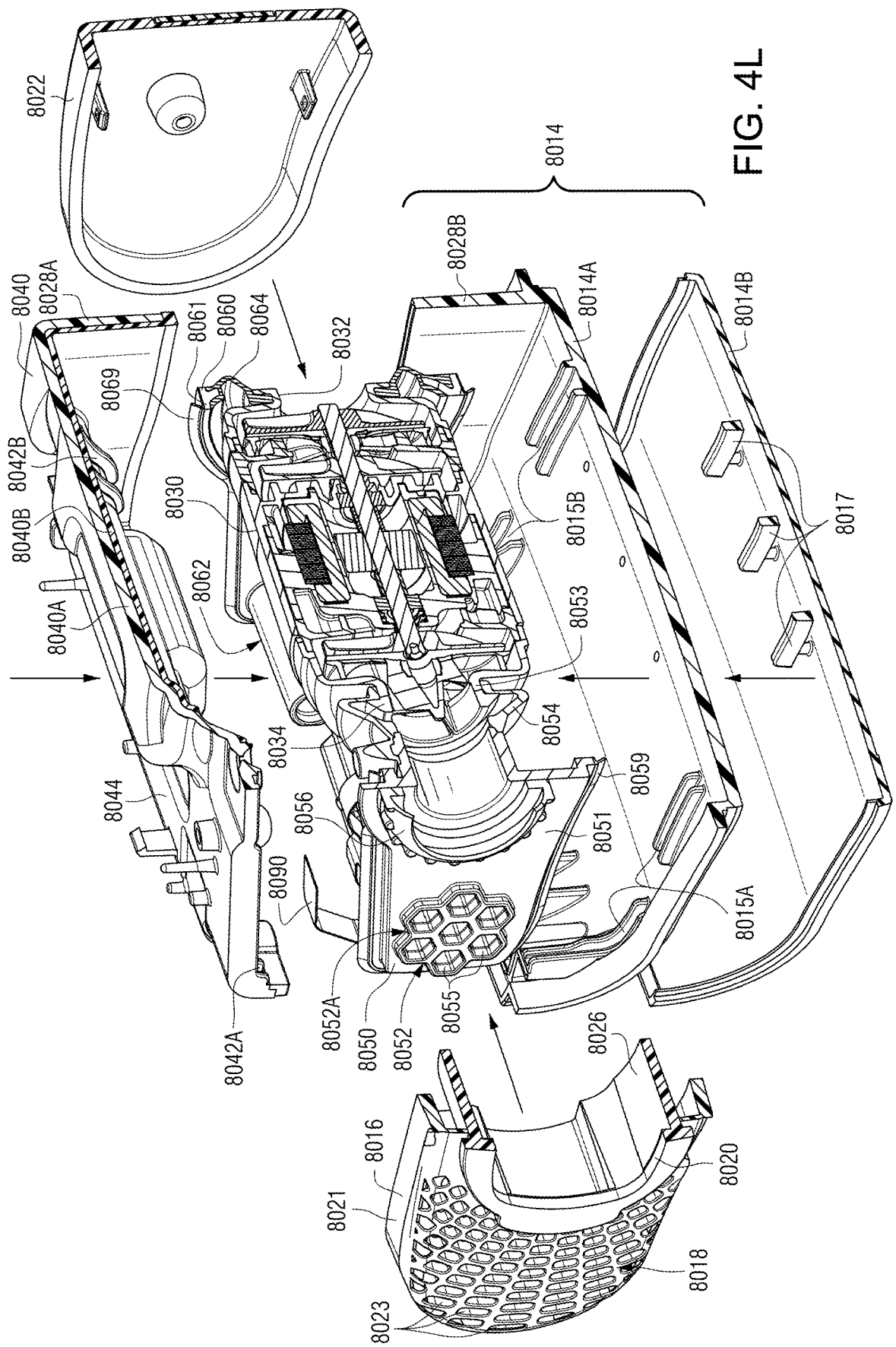

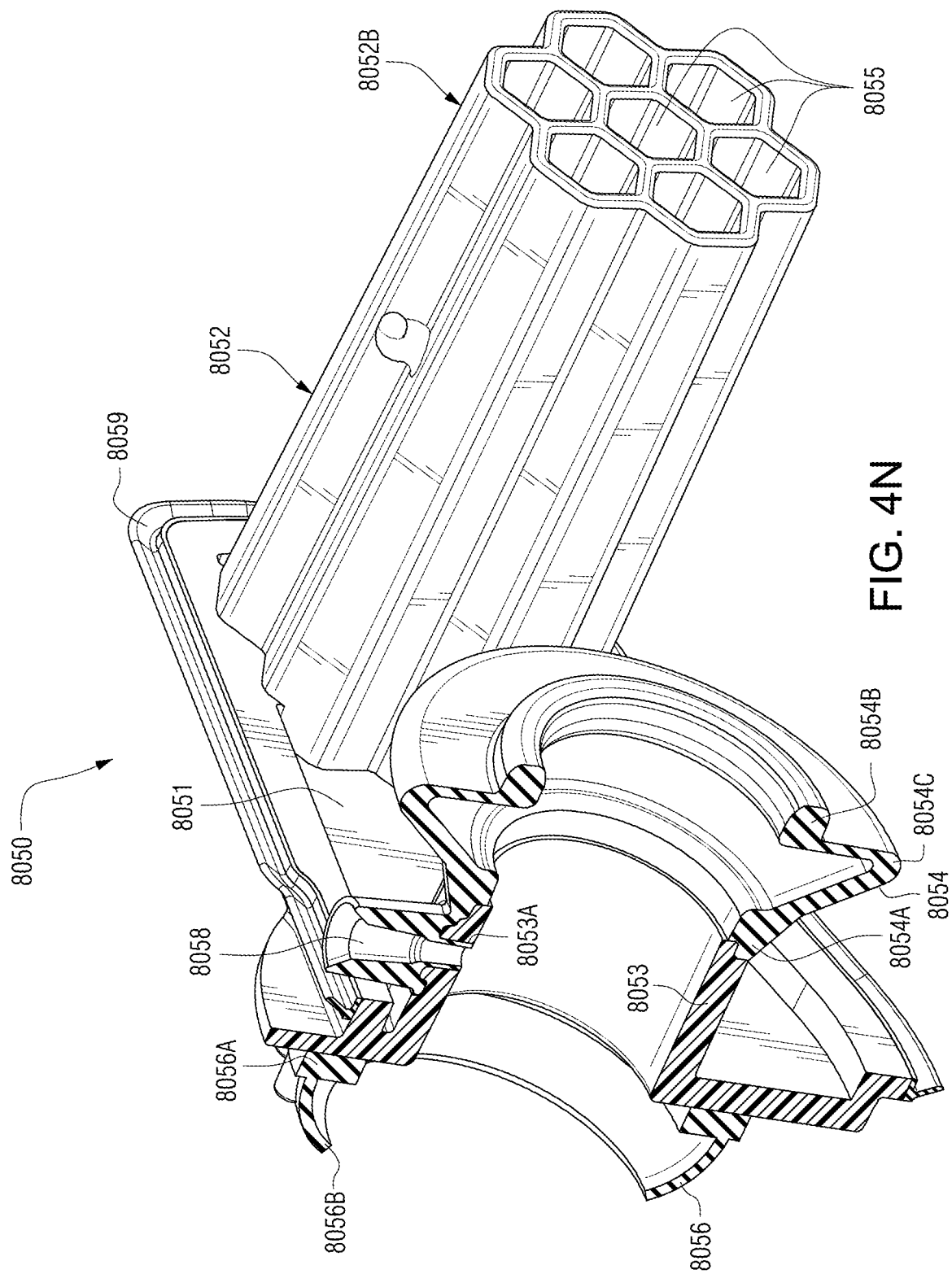

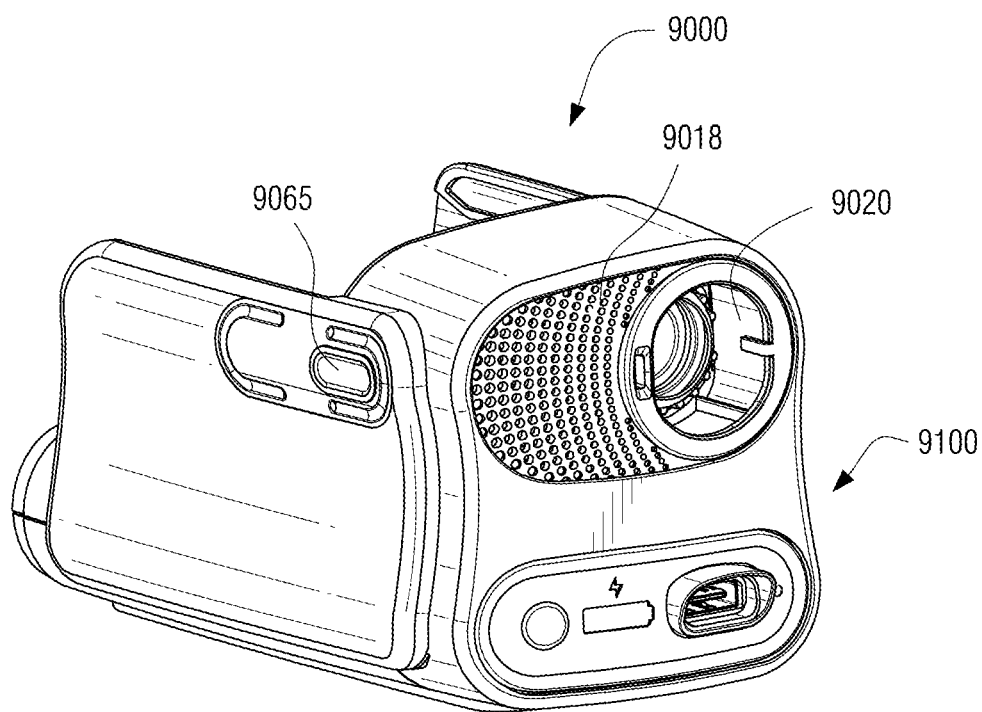
Fig. 4W1
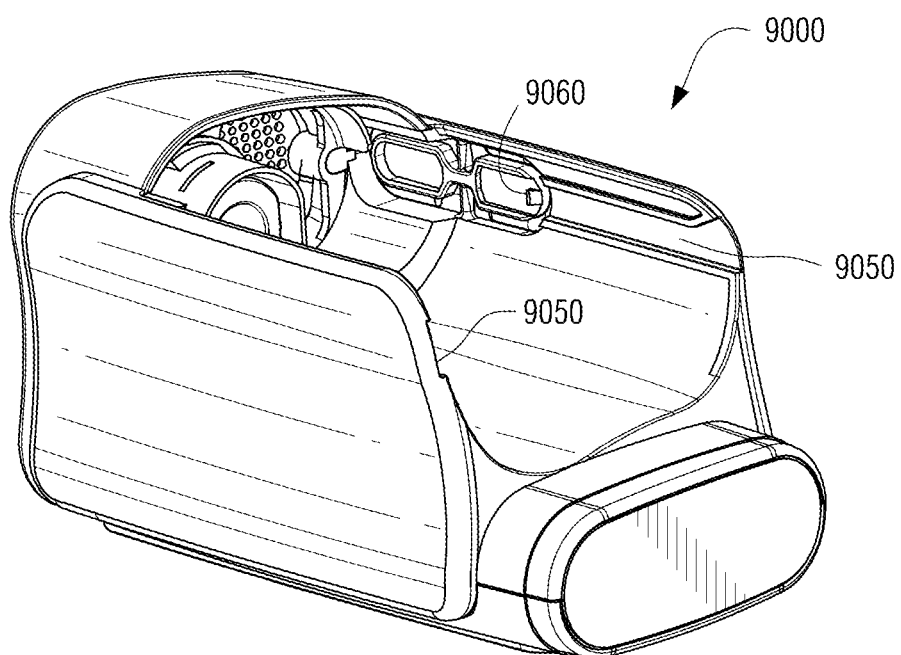
Fig. 4W2

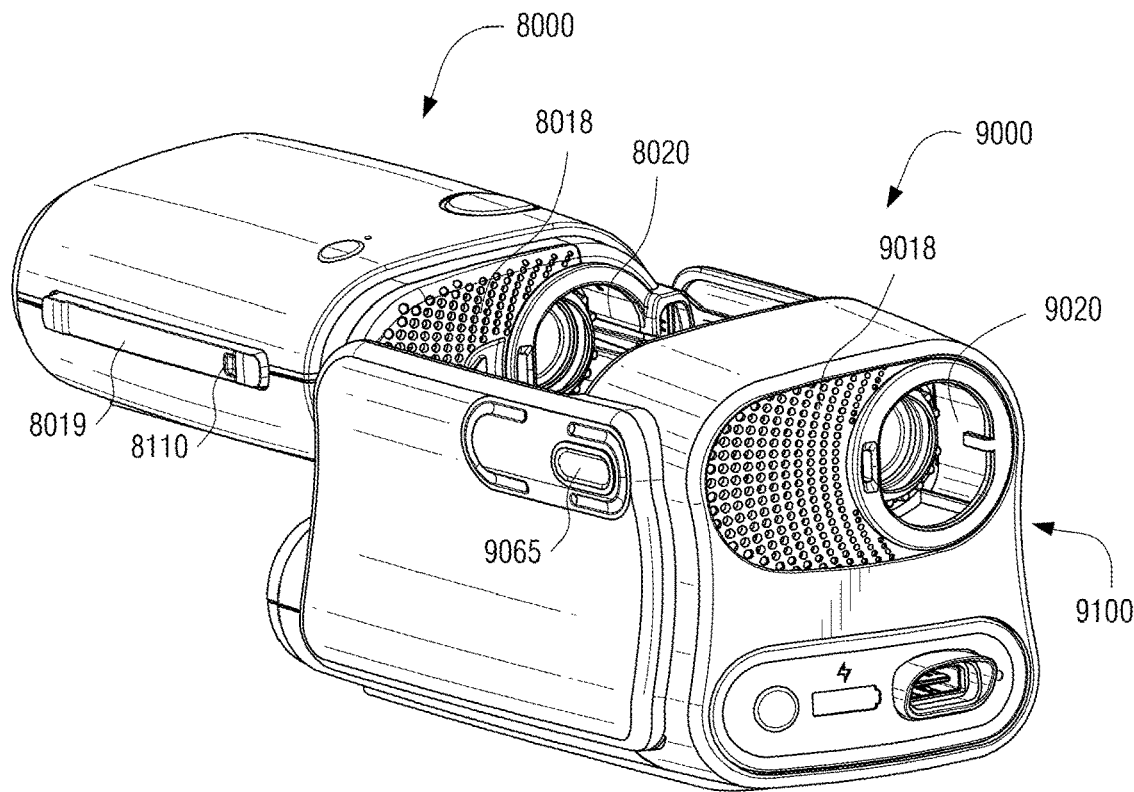
Fig. 4X1
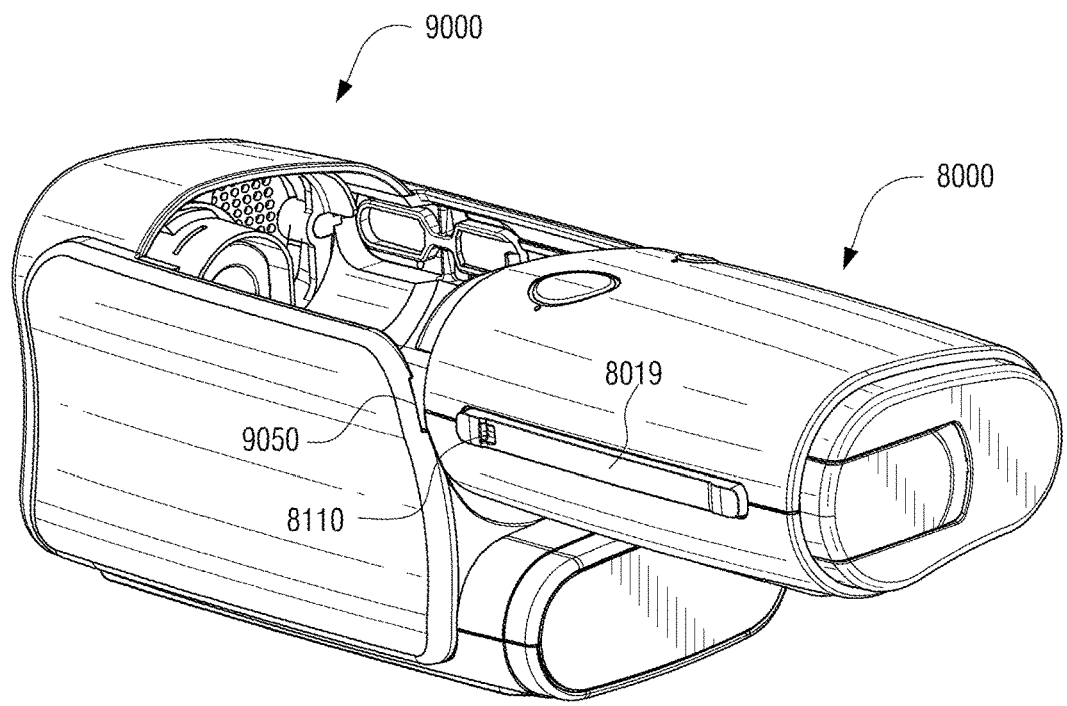
Fig. 4X2

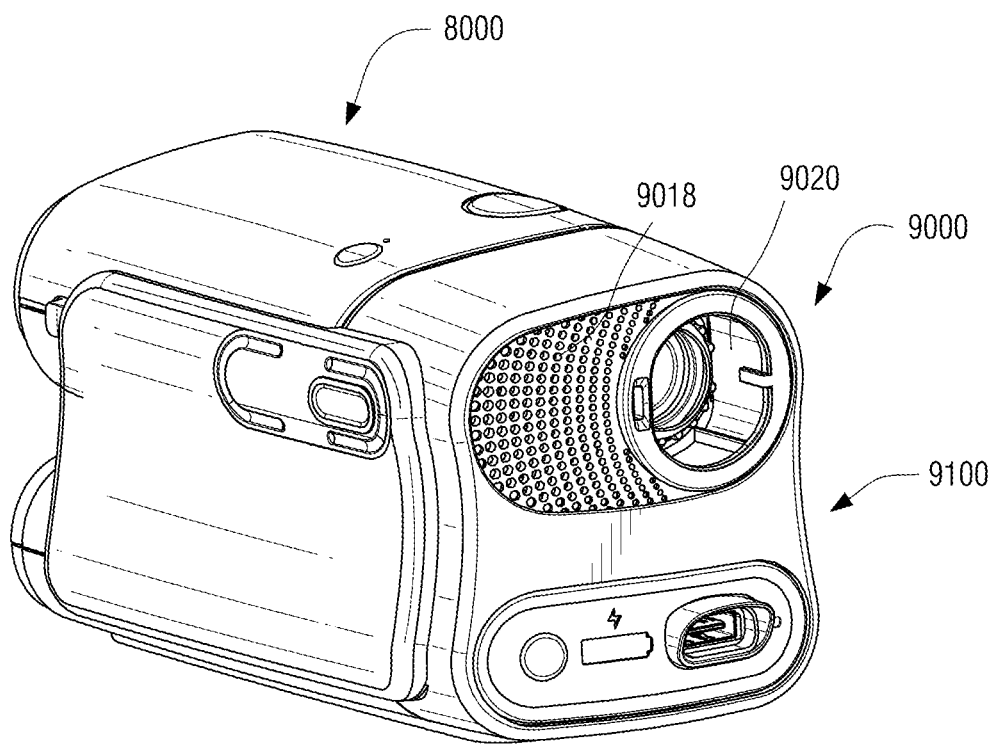
Fig. 4Y1
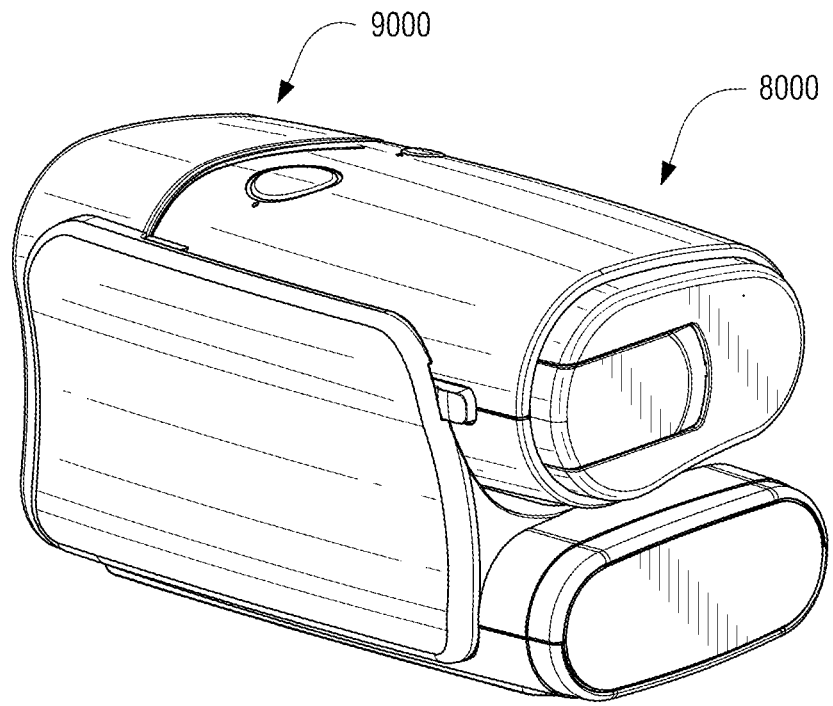
Fig. 4Y2

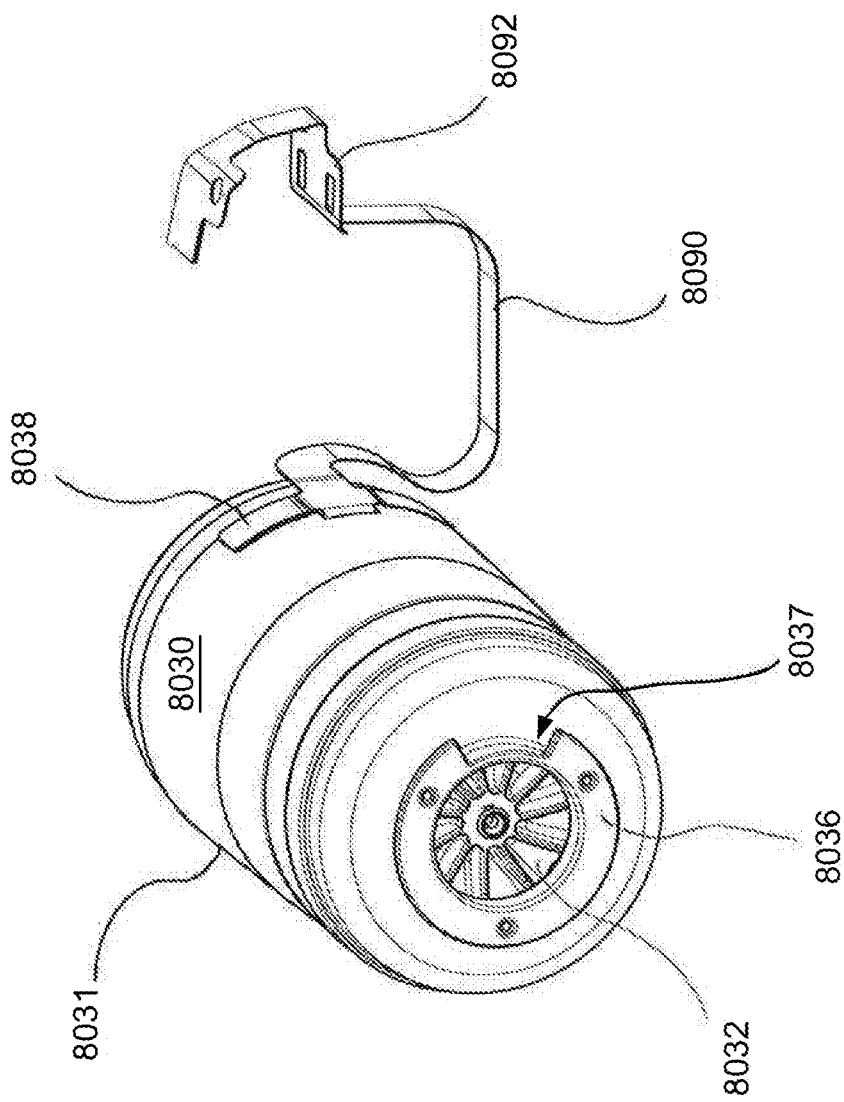
FIG. 4Z1

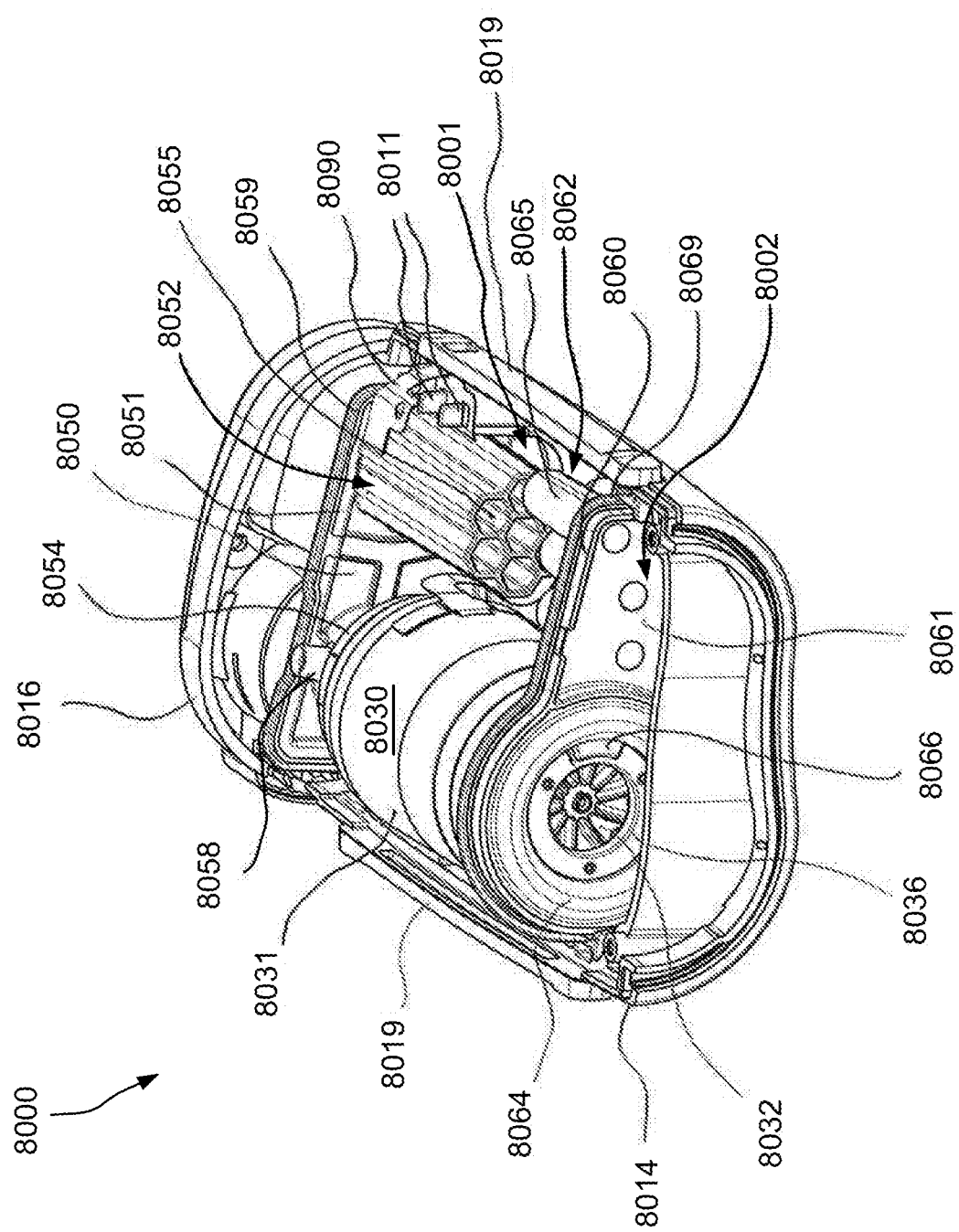
FIG. 4ZZ2

RESPIRATORY PRESSURE THERAPY DEVICE

1 CROSS-REFERENCE TO RELATED APPLICATIONS

This application claims the benefit of U.S. Provisional Application No. 62/307,882, filed Mar. 14, 2016, which is incorporated herein by reference in its entirety.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory insufficiency, in forms such as OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used underwater swimming or diving may be configured to guard against ingress of water from an external higher pressure, but not to maintain air internally at a higher pressure than ambient.

Certain masks may be impractical for use while sleeping, e.g. for sleeping while lying on one's side in bed with a head on a pillow.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

2.2.3.2 Vent Technologies

Some forms of respiratory treatment systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O) Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.3 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology relates to an RPT device structured and configured to reduce noise output, e.g., while maintaining a relatively small size.

An aspect of the present technology relates to an RPT device including an inlet having a plurality of inlet tubes, e.g., arranged in an array, to reduce noise output.

An aspect of the present technology relates to apparatus for generating a supply of air at positive pressure for the amelioration or treatment of a respiratory disorder, the apparatus comprising a housing, a blower positioned in the housing, the blower being structured and configured to produce a flow of air at positive pressure, a flexible connector electrically and physically connected to the blower, and a blower rotation limitation structure configured to reduce rotation of the blower during use. The blower rotation limitation structure may comprise a first rotation limitation member provided on the first blower suspension, the first rotation limitation member interacting in use with a second rotation limitation member provided on the blower to limit rotation of the blower. In one example, the first rotation limitation member comprises a notch on the blower and the second rotation limitation member comprises a tongue provided to the first blower suspension, the notch and tongue being configured to engage with each other to limit rotation of the blower.

Another aspect of the present technology relates to apparatus for generating a supply of air at positive pressure for the amelioration or treatment of a respiratory disorder, the apparatus comprising a housing, a blower positioned in the housing, the blower being structured and configured to produce a flow of air at positive pressure, a first blower suspension structured and configured to support a first end of the blower adjacent a blower outlet of the blower, a second blower suspension structured and configured to support a second end of the blower adjacent a blower inlet of the blower, the second end being at an opposite end of the blower to the first end, and a blower rotation limitation structure configured to reduce rotation of the blower during use. In an example, the apparatus comprises a first plate assembly and a second plate assembly, wherein the first plate assembly comprises the first blower suspension and a first base plate and the second blower assembly comprises the second blower suspension and a second base plate.

Another aspect of the present technology relates to apparatus for generating a supply of air at positive pressure for the amelioration or treatment of a respiratory disorder, the apparatus comprising a housing, a blower positioned in the housing, the blower being structured and configured to produce a flow of air at positive pressure, a flexible connector electrically and physically connected to the blower, and one or more connector anchors for anchoring a longitudinal middle section of the flexible connector to another part of the apparatus.

Another aspect of the present technology relates to apparatus for generating a supply of air at positive pressure for the amelioration or treatment of a respiratory disorder, the apparatus comprising a housing, a blower positioned in the housing, the blower being structured and configured to produce a flow of air at positive pressure, a blower suspension to support the blower, wherein the blower suspension is flexible and in tension.

An aspect of certain forms of the present technology is a medical device that is easy to use, e.g. by a person who does not have medical training, by a person who has limited dexterity or by a person with limited experience in using this type of medical device.

An aspect of one form of the present technology is a portable RPT device that may be carried by a person, e.g., around the home of the person.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 2:
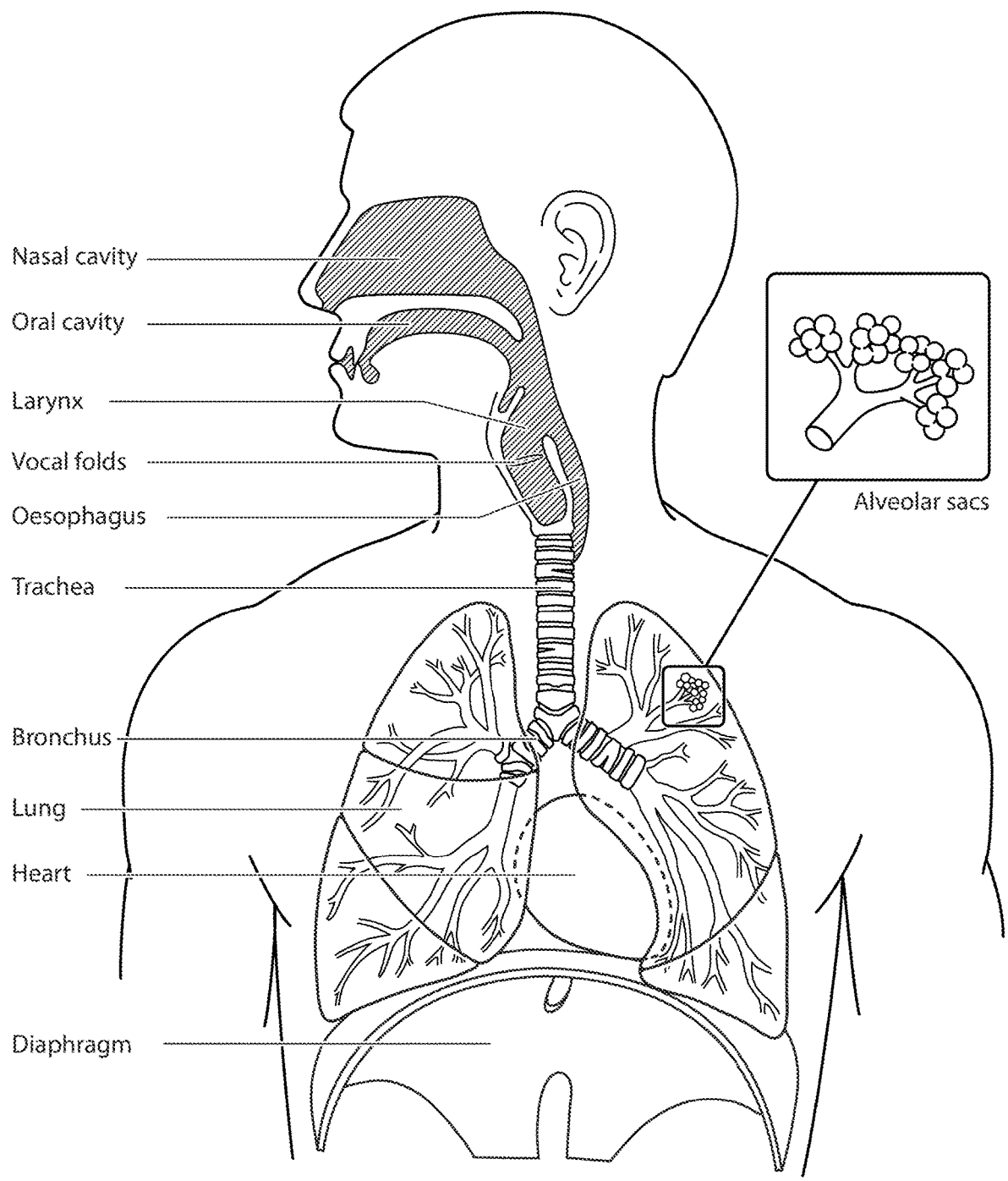

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

Figure 3:
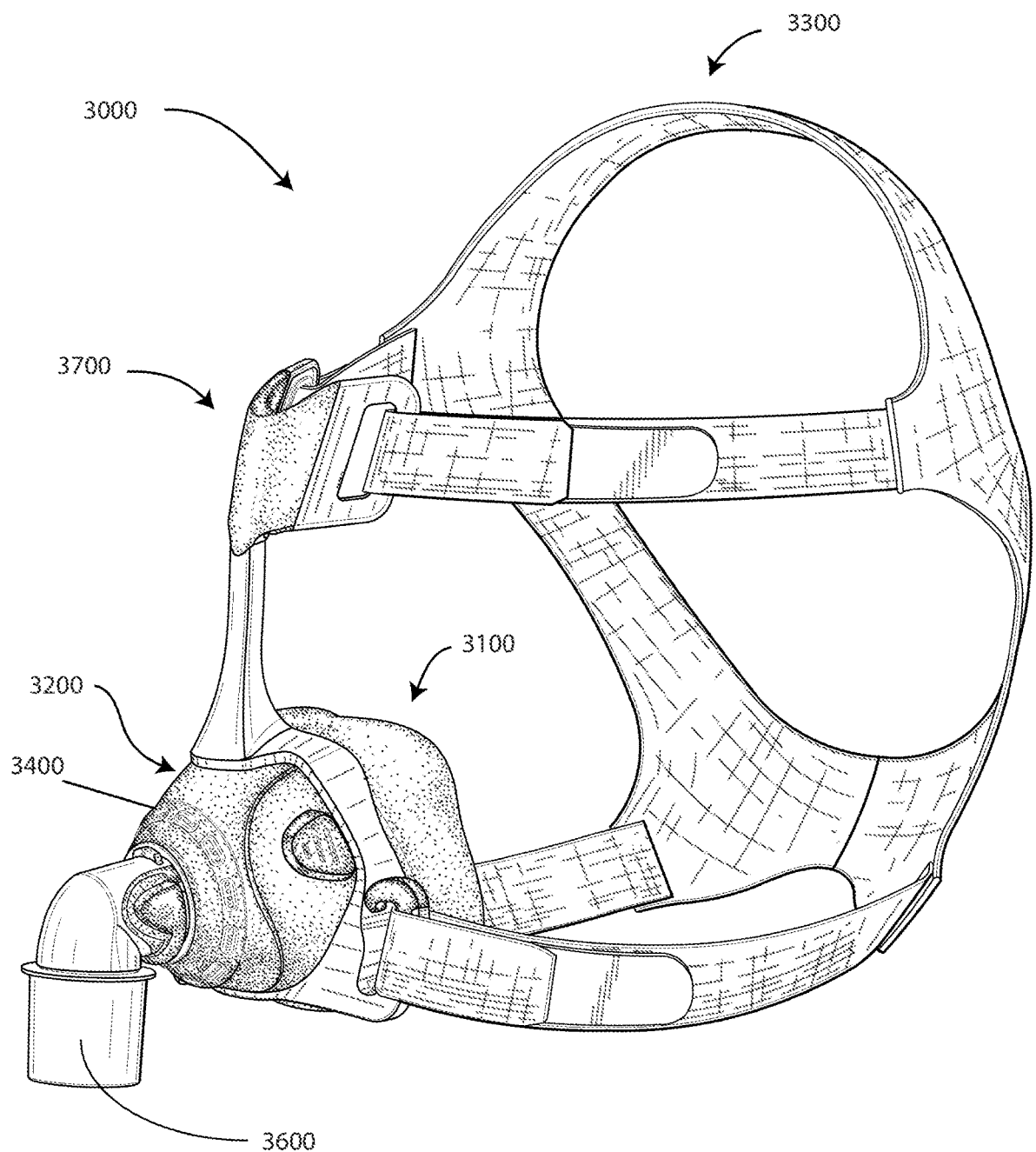

FIG. 3 shows a patient interface in the form of a nasal mask in accordance with one form of the present technology.

4.4 RPT Device

Figure 4A:
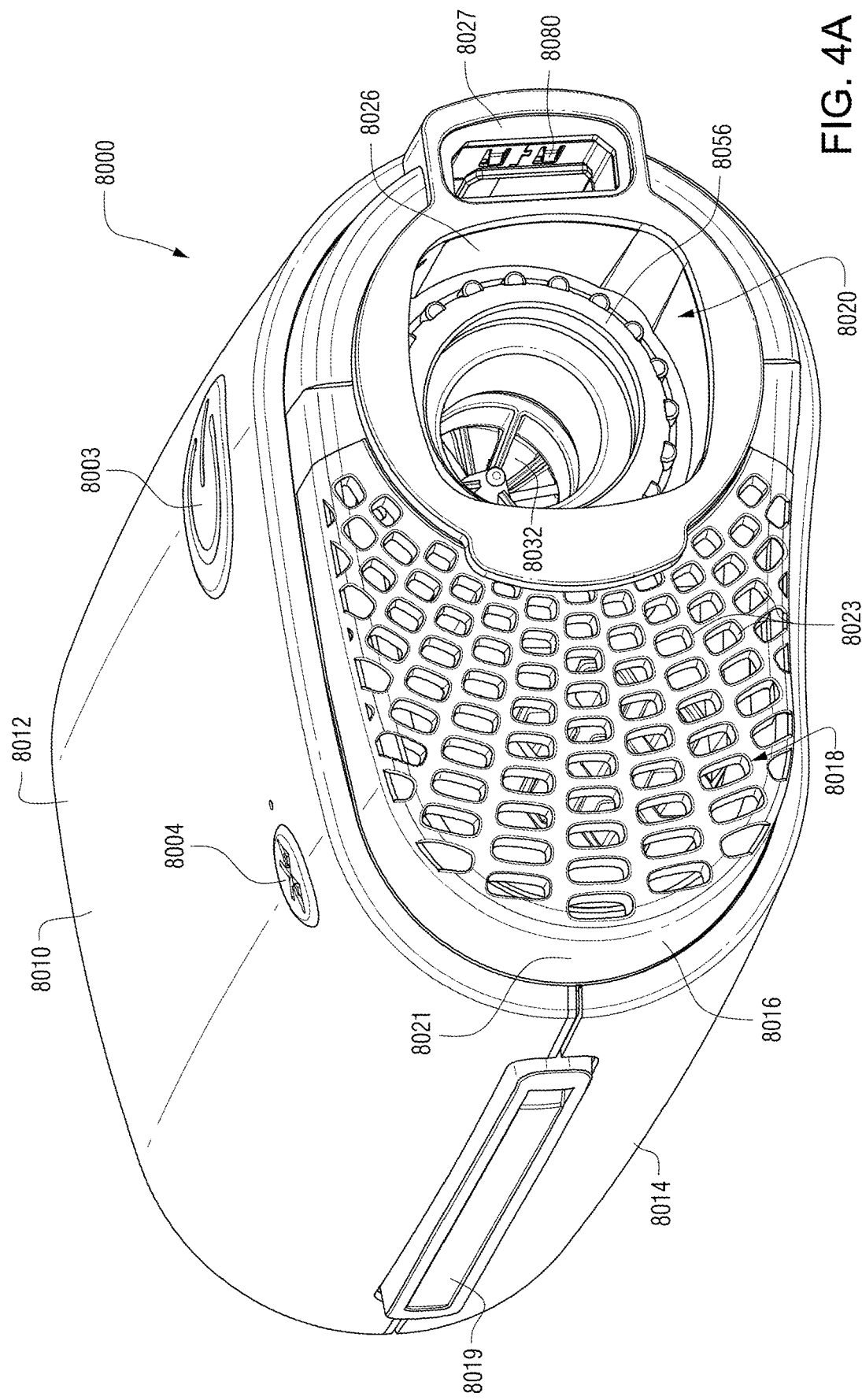

FIG. 4A is a perspective view of an RPT device in accordance with one form of the present technology.

Figure 4B:
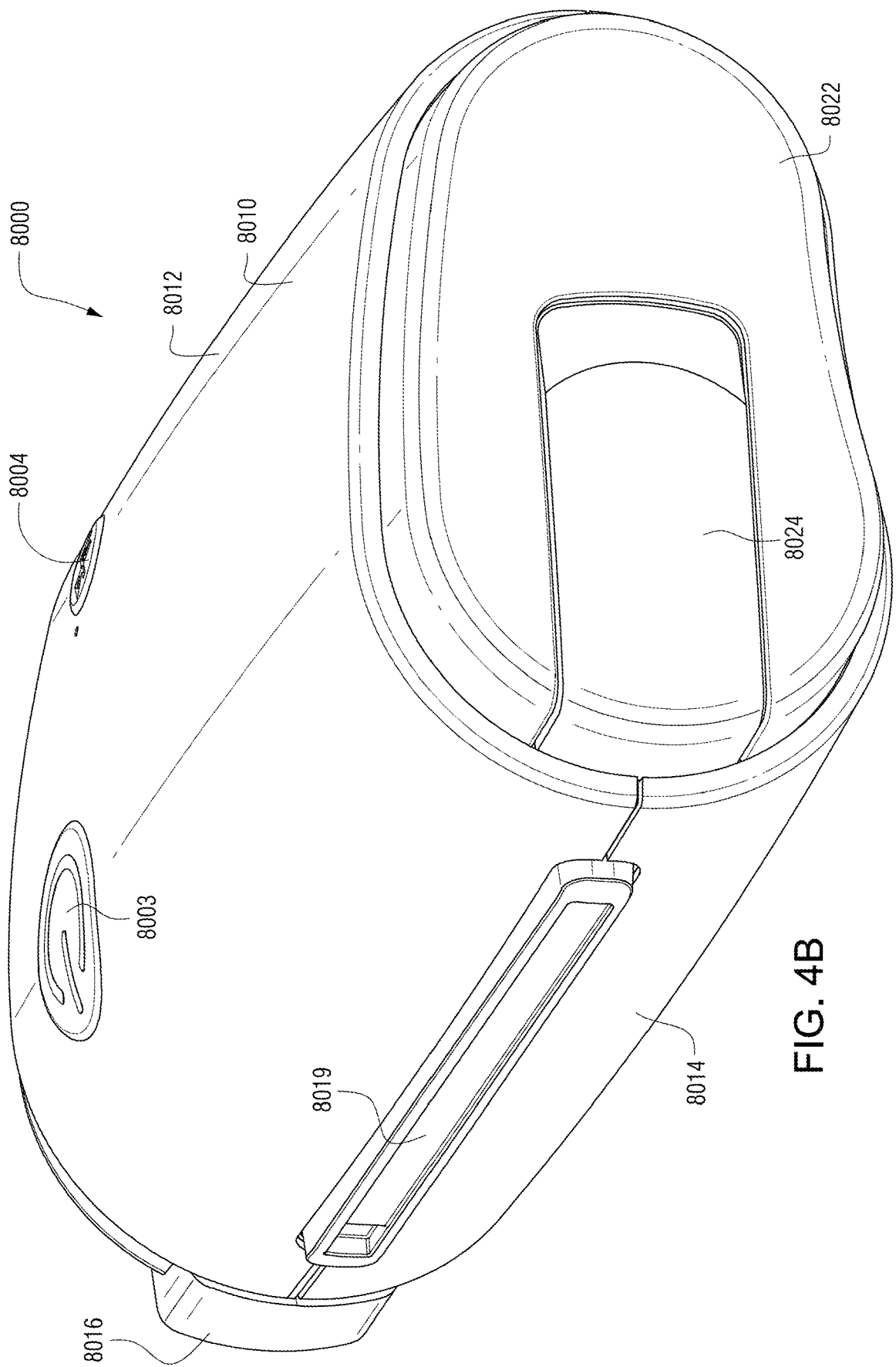

FIG. 4B is another perspective view of the RPT device of FIG. 4A.

Figure 4C:
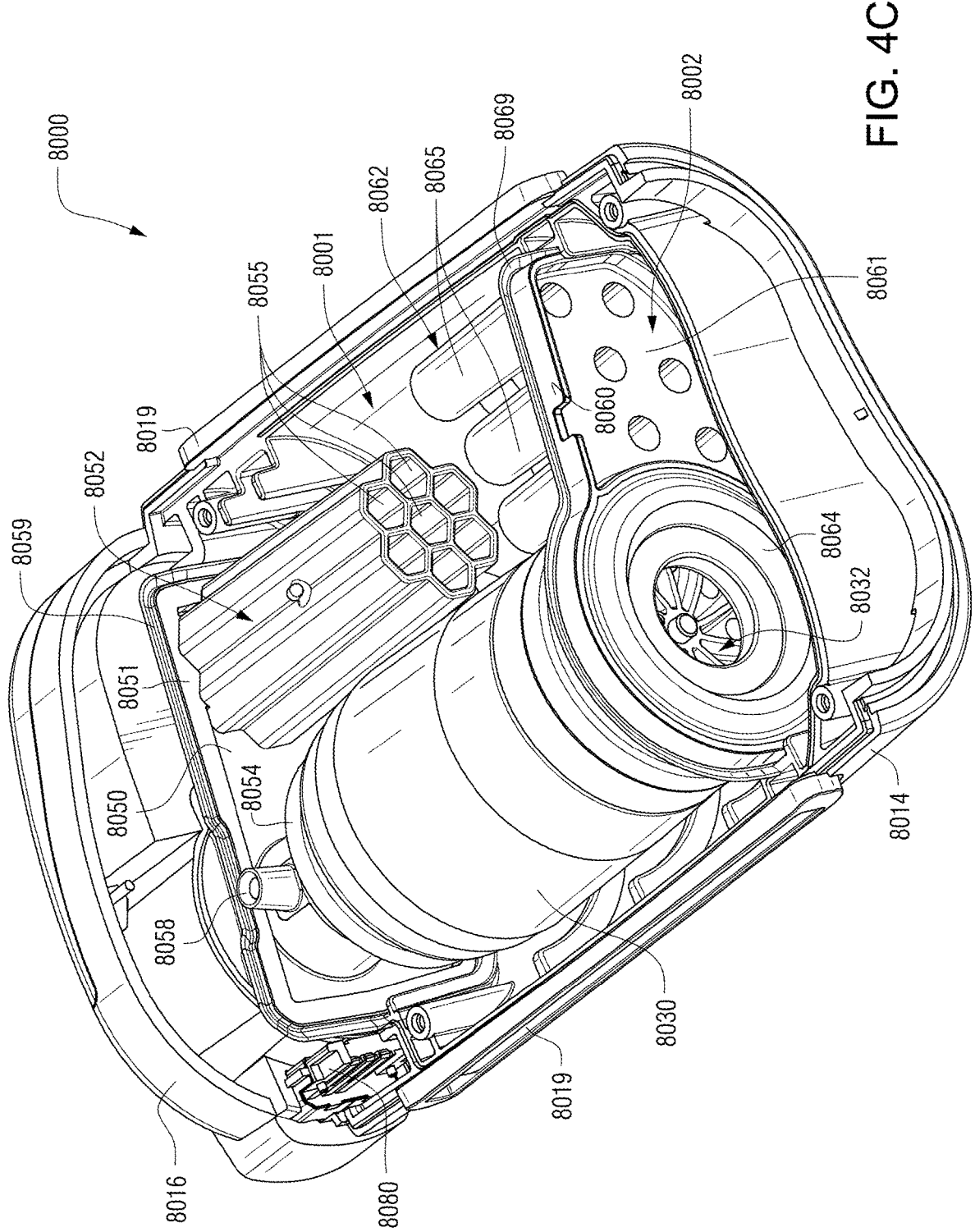

FIG. 4C is a perspective view of the RPT device of FIG. 4A, with an intermediate cover and portions of the housing removed.

Figure 4D:
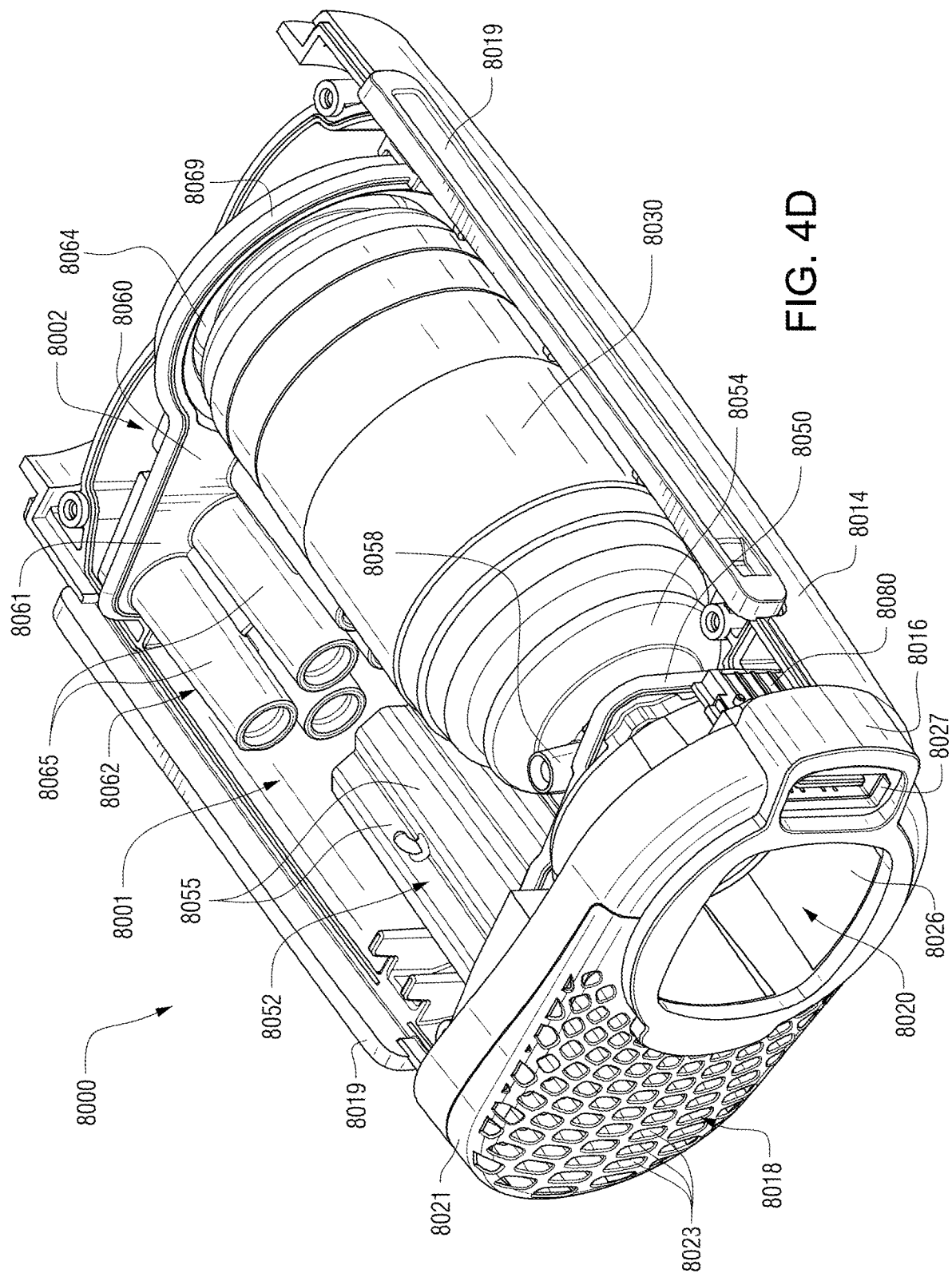

FIG. 4D is another perspective view of the RPT device of FIG. 4A, with an intermediate cover and portions of the housing removed.

Figure 4E:
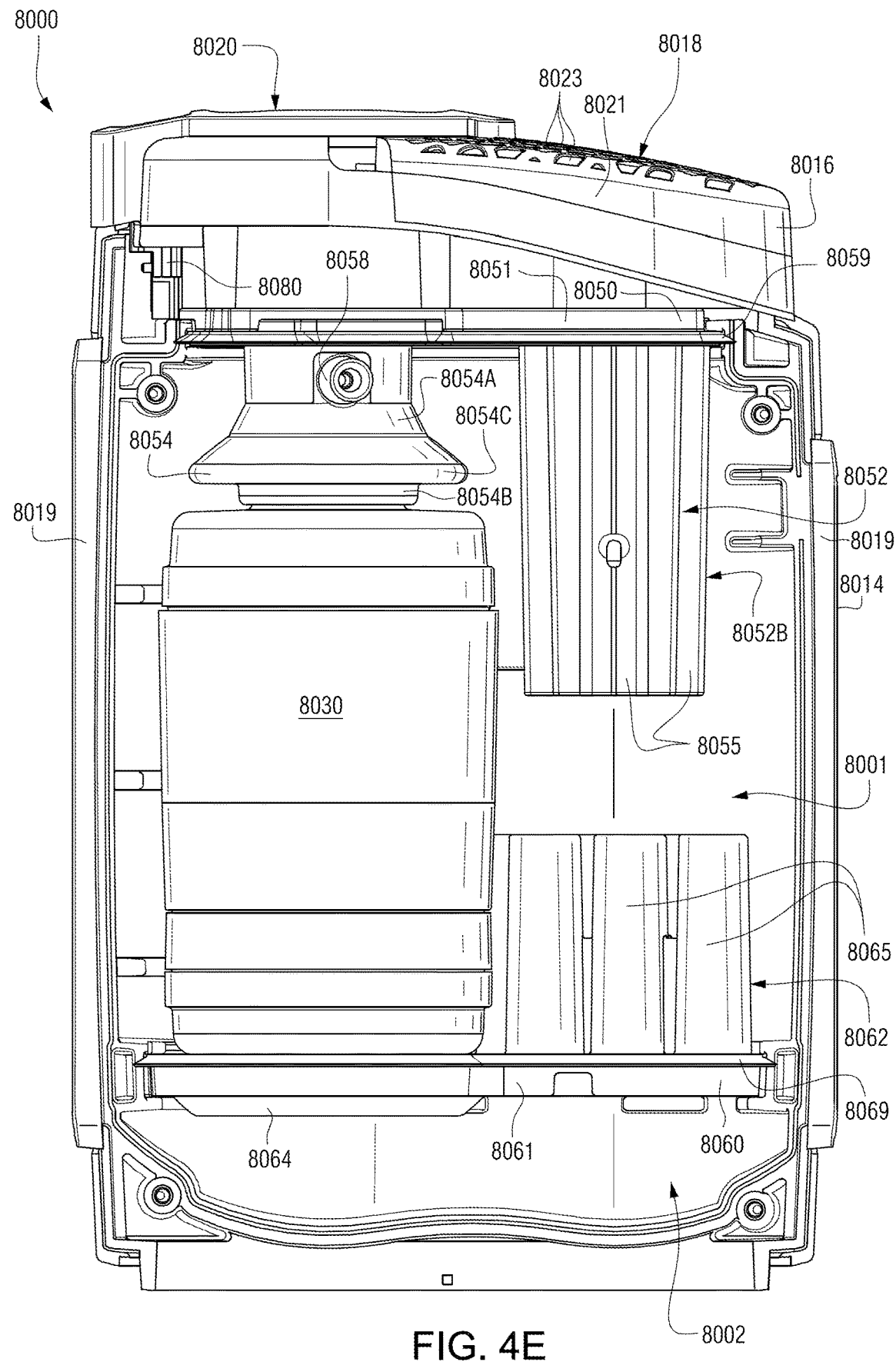

FIG. 4E is a top view of the RPT device of FIG. 4A, with an intermediate cover and portions of the housing removed.

FIG. 4F is an exploded view of components of the RPT device shown in FIGS. 4C to 4E.

Figure 4G:
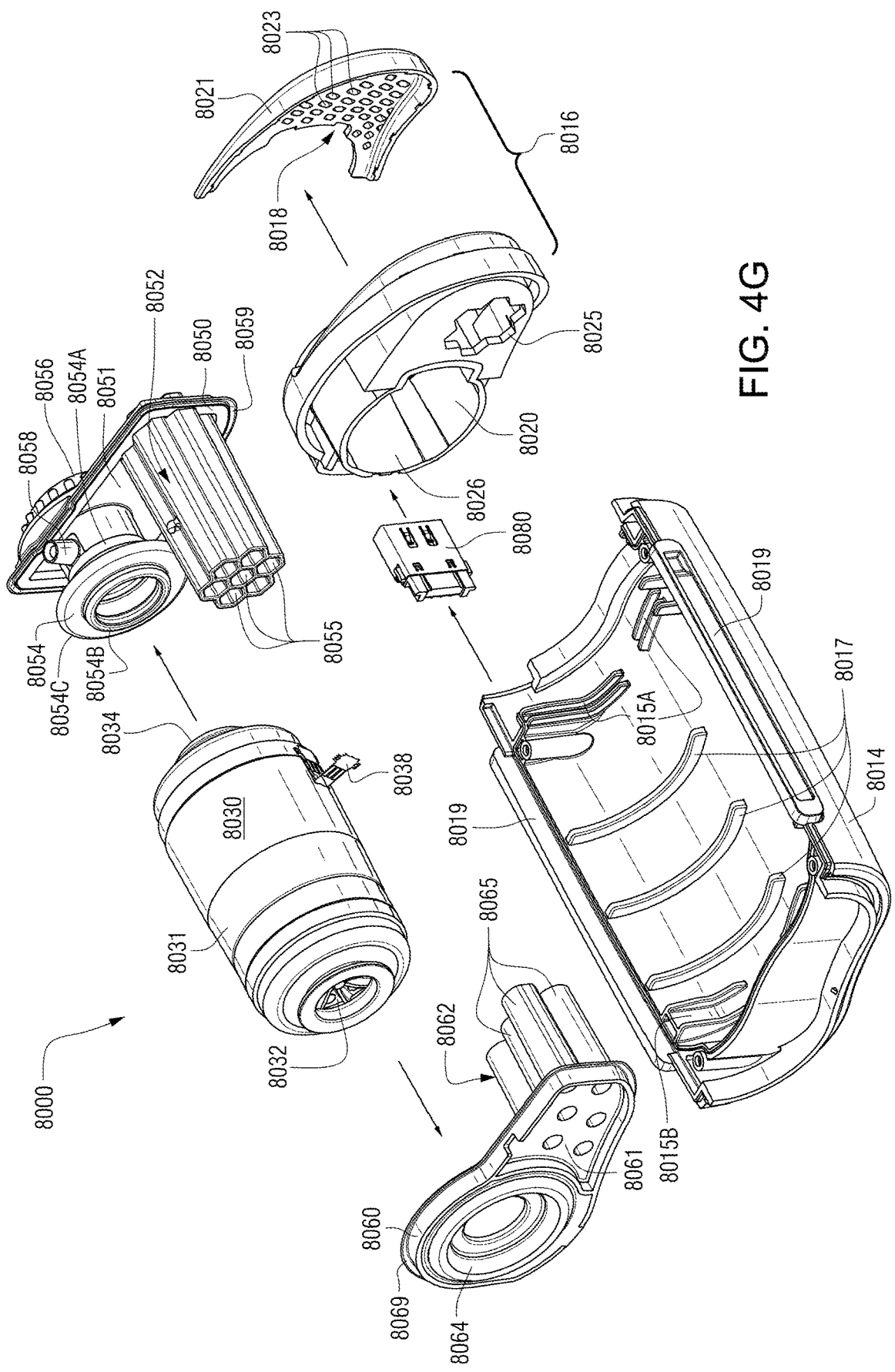

FIG. 4G is a further exploded view of components of the RPT device shown in FIGS. 4C to 4E.

Figure 4H:
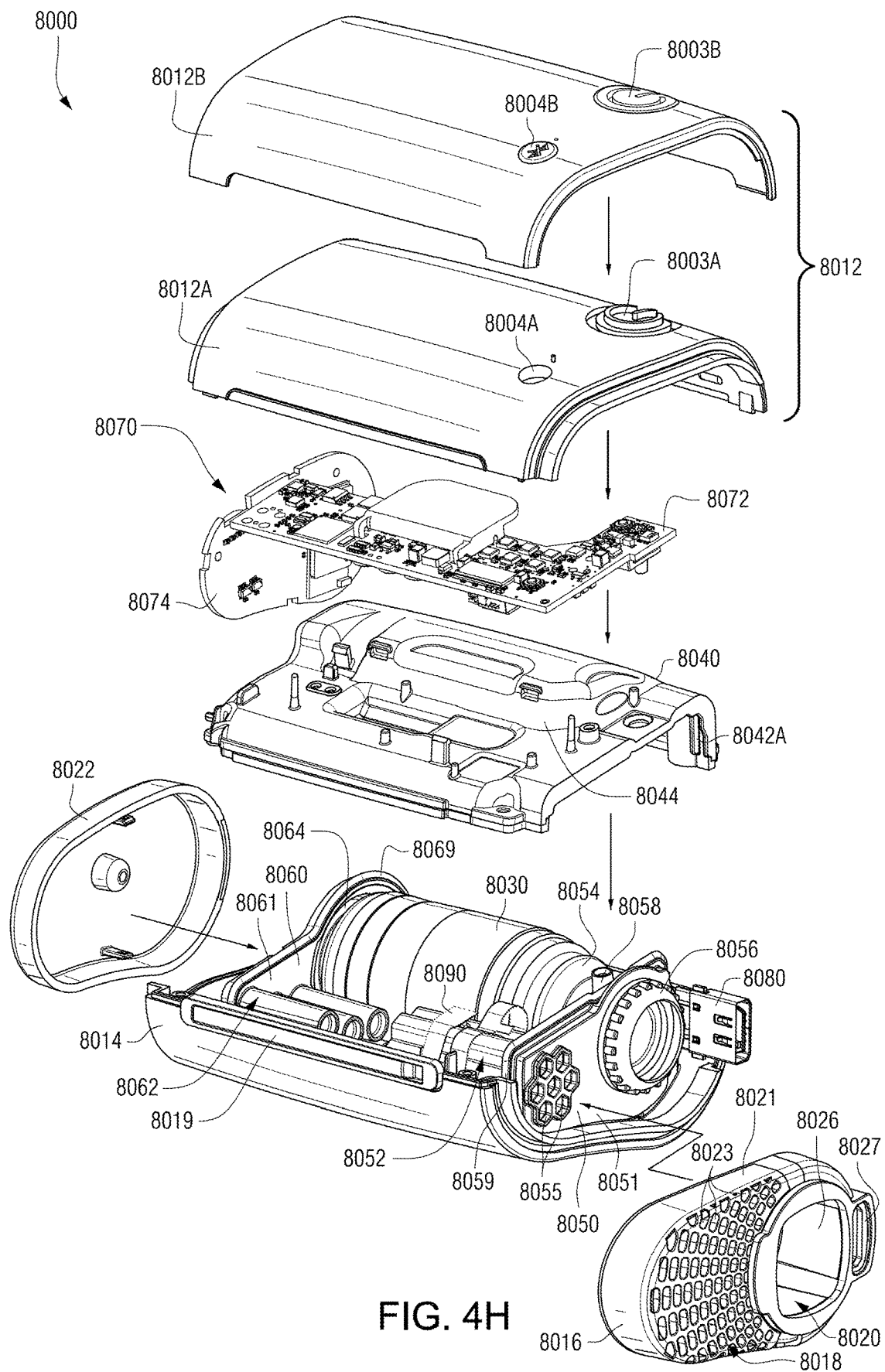

FIG. 4H is an exploded view of the RPT device shown in FIG. 4A.

Figure 4I:
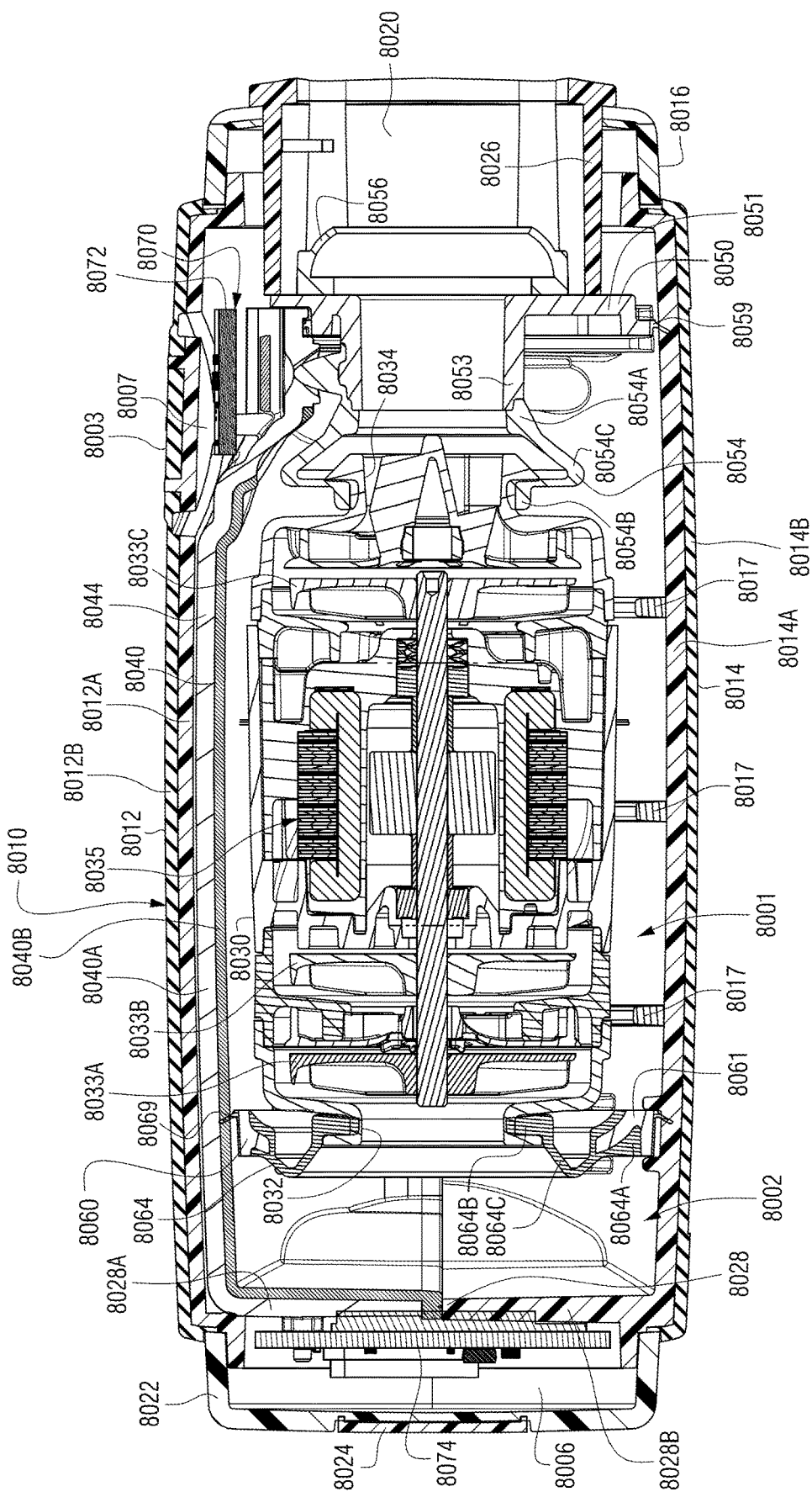

FIG. 4I is a cross-sectional view of the RPT device shown in FIG. 4A.

Figure 4J:
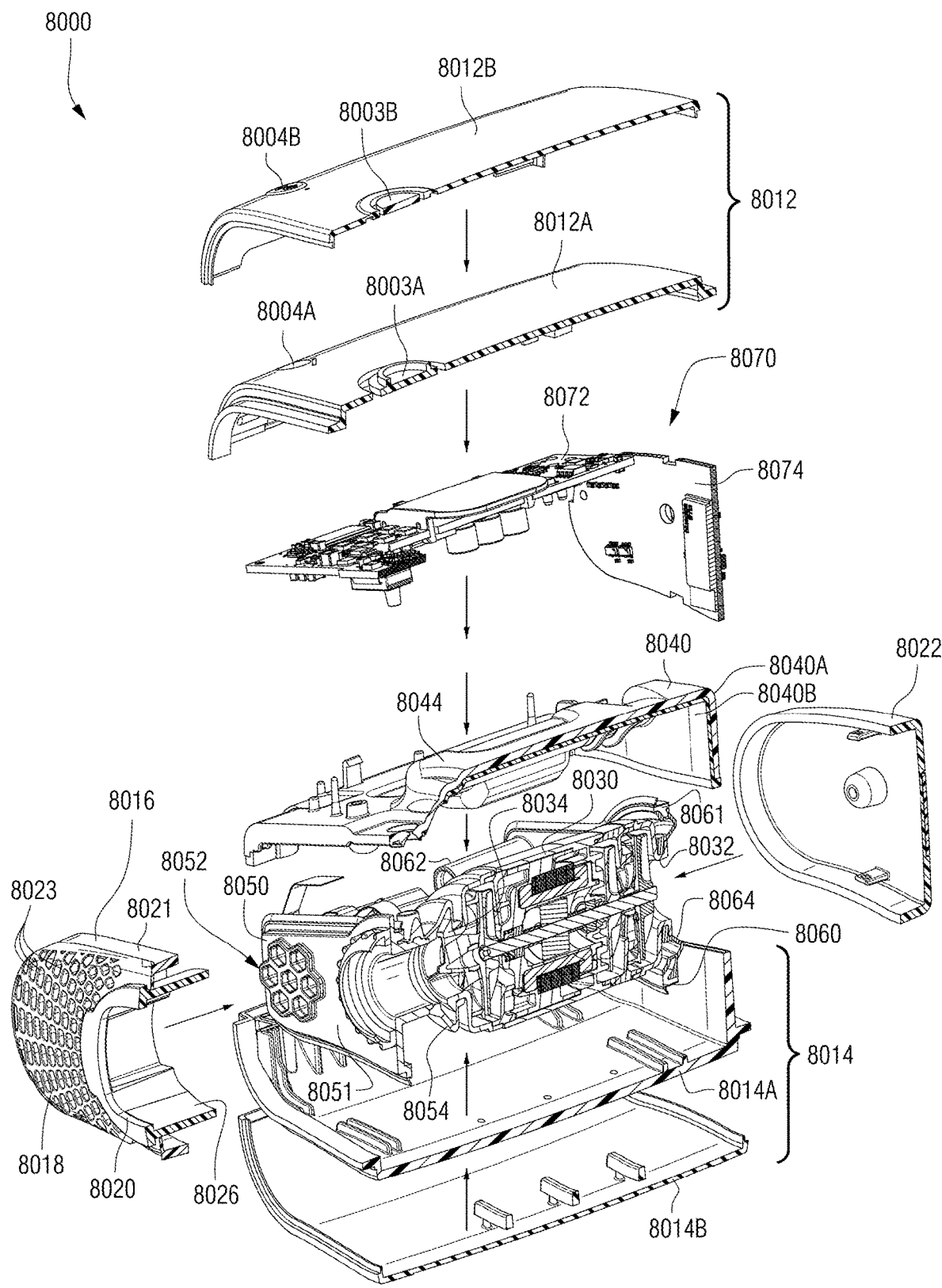

FIG. 4J is an exploded and cross-sectional view of the RPT device shown in FIG. 4A.

Figure 4K:
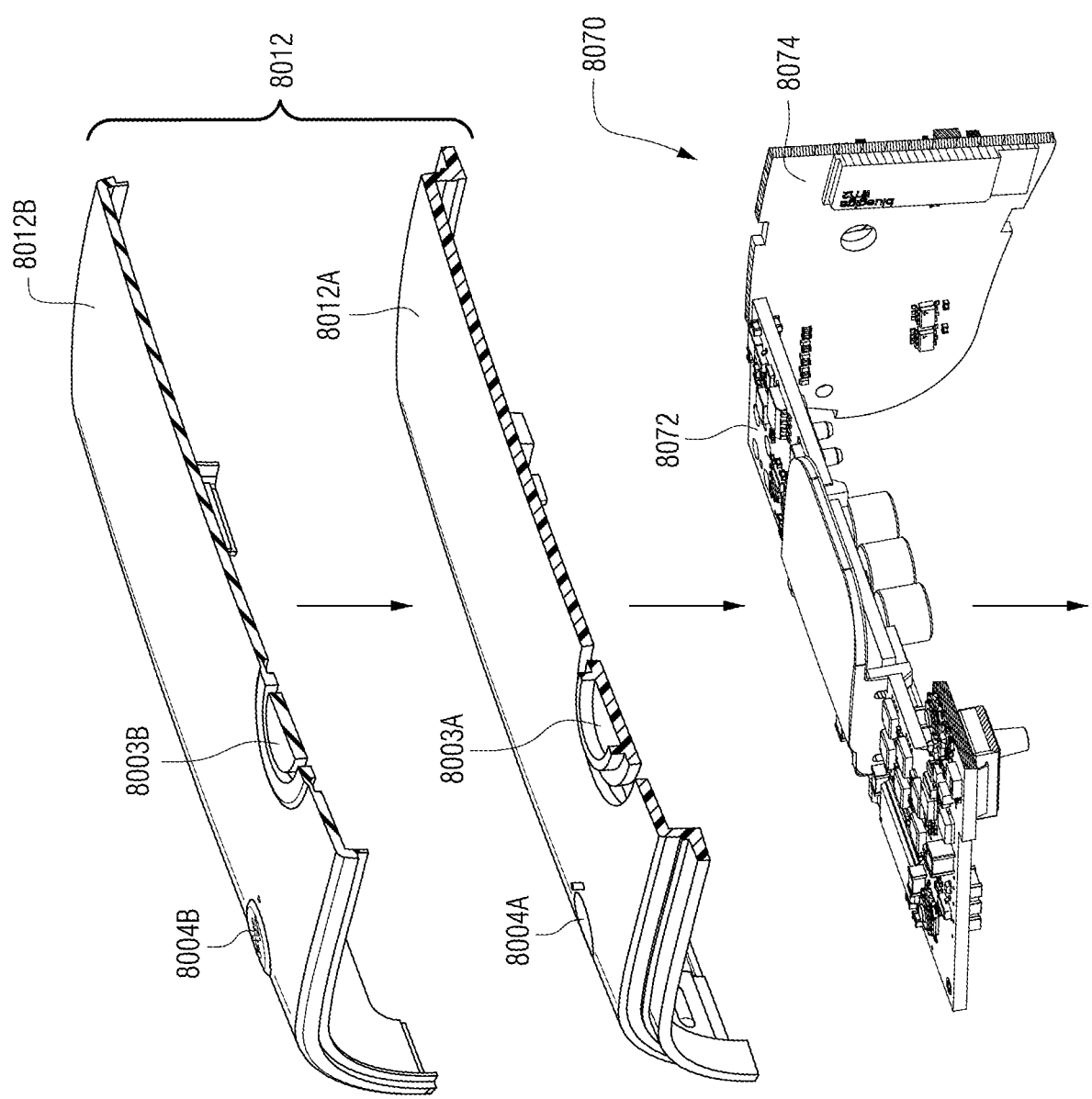

FIG. 4K is an enlarged portion of the RPT device of FIG. 4J.

FIG. 4L is an enlarged portion of the RPT device of FIG. 4J.

Figure 4M:
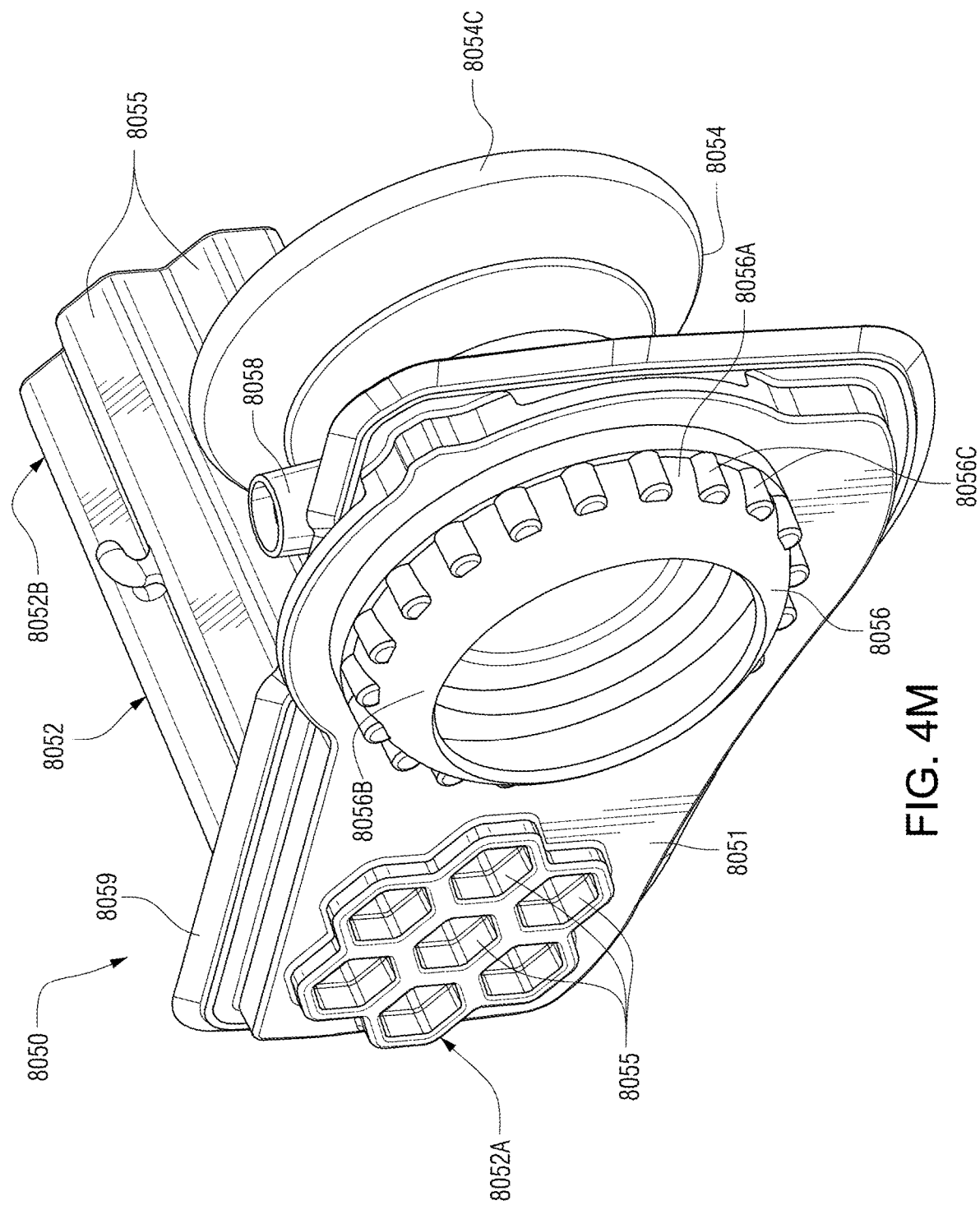
Figure 40:
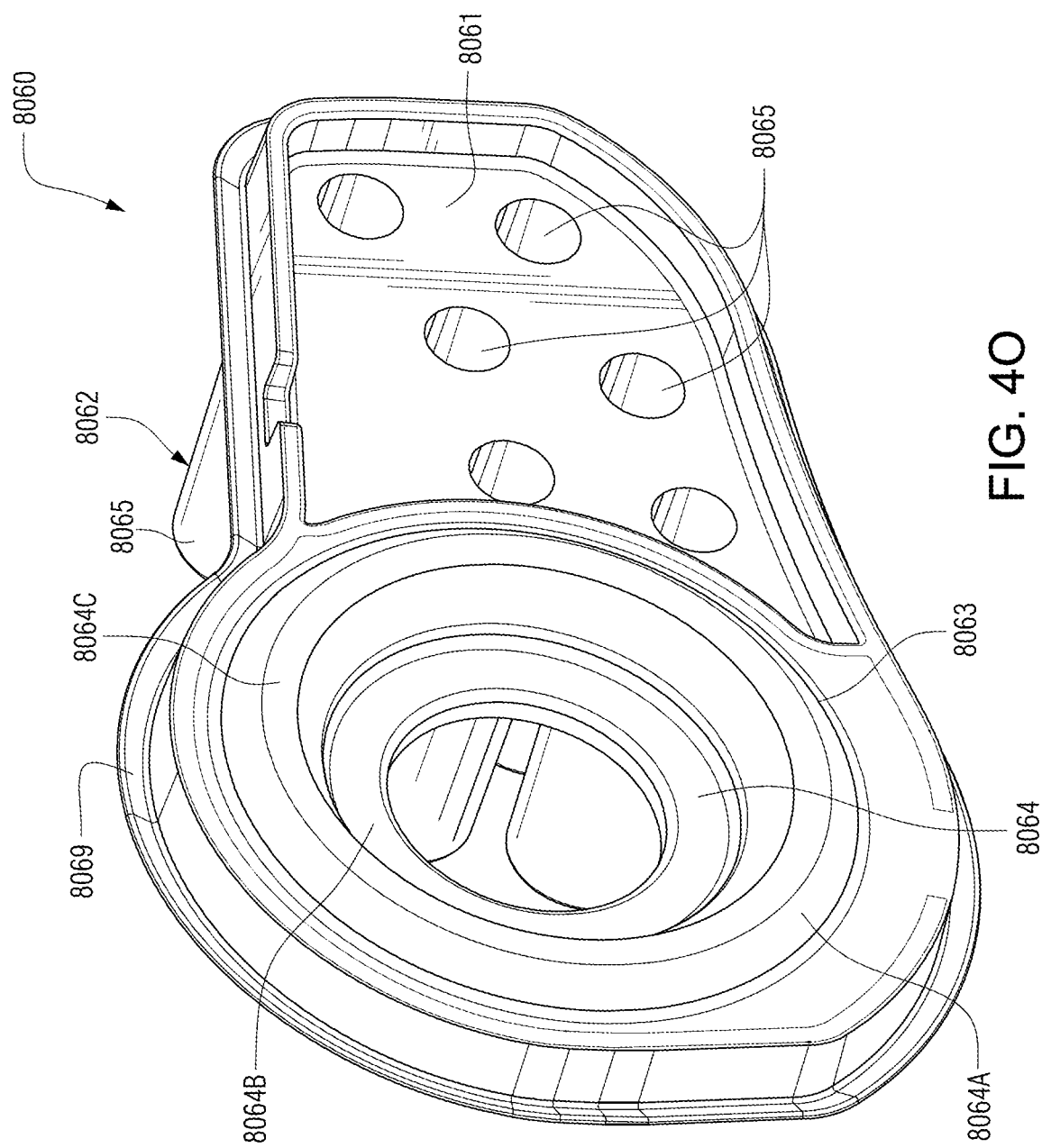

FIG. 4M is a perspective view of a first plate assembly for an RPT device in accordance with one form of the present technology.

FIG. 4N is a cross-sectional view of the first plate assembly shown in FIG. 4M.

FIG. 4O is a perspective view of a second plate assembly for an RPT device in accordance with one form of the present technology.

Figure 4P:
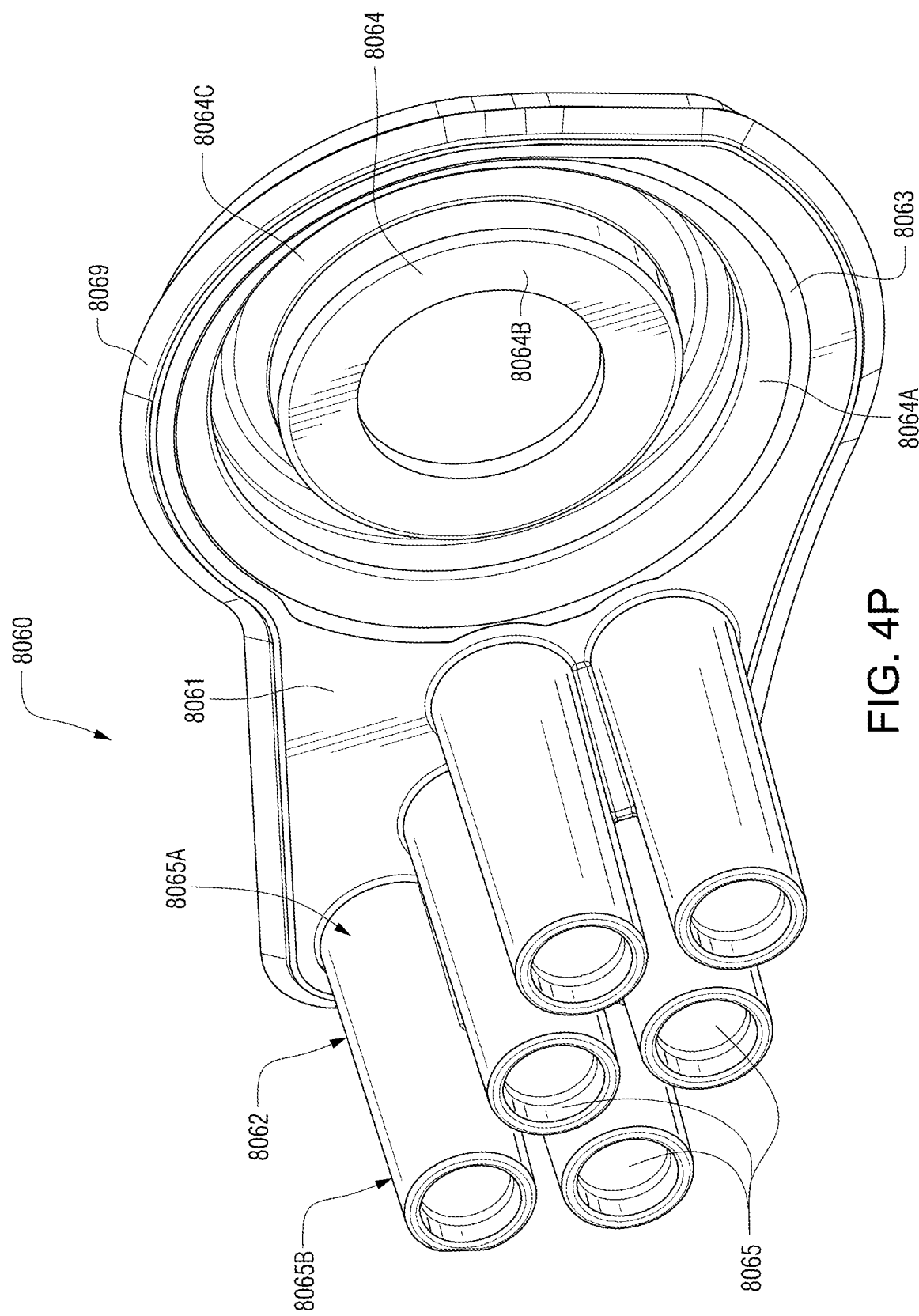

FIG. 4P is another perspective view of the second plate assembly shown in FIG. 4O.

Figure 4Q:
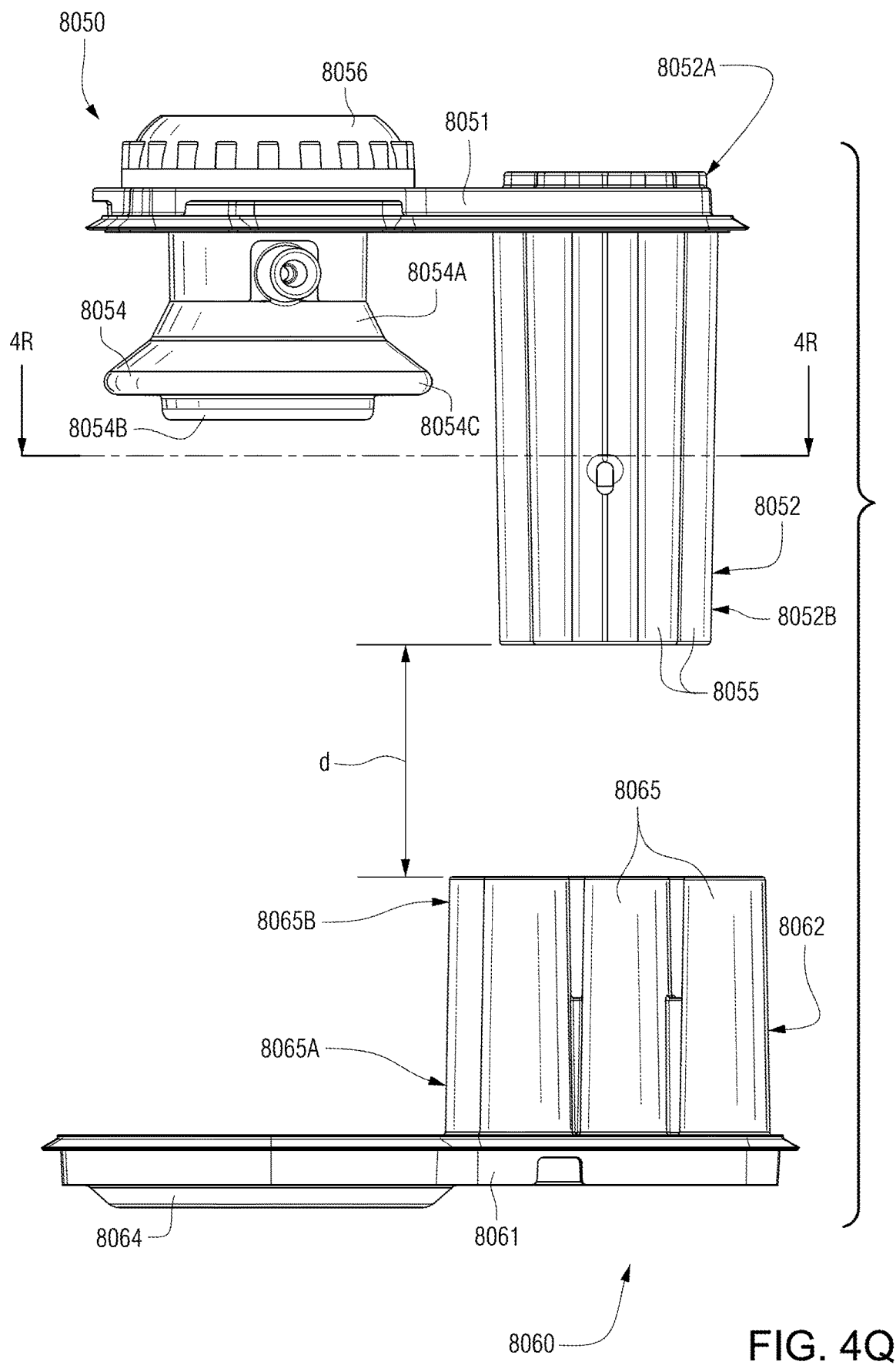

FIG. 4Q is a top view showing the arrangement of first and second plate assemblies for an RPT device in accordance with one form of the present technology.

Figure 4R:
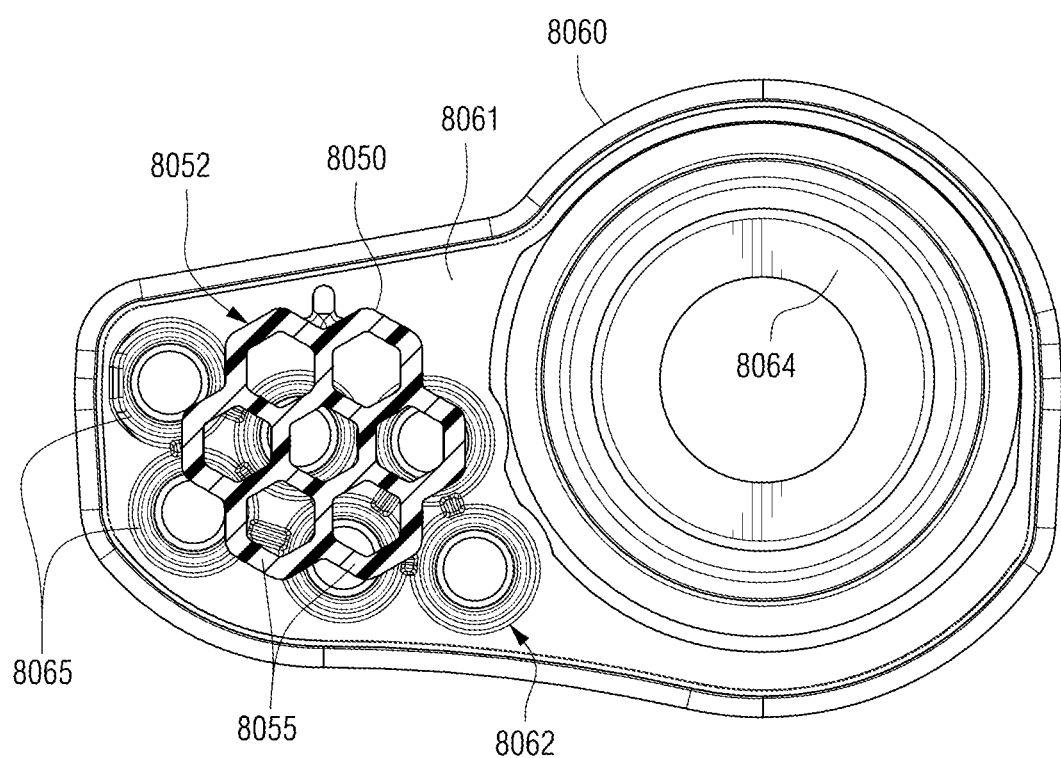

FIG. 4R is a cross-sectional view through line 4R-4R of FIG. 4Q.

Figure 4S:
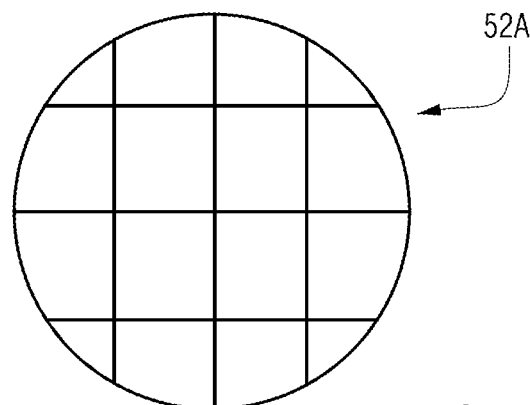

FIG. 4S is a schematic view of an inlet tube array for an RPT device in accordance with one form of the present technology.

Figure 4T:
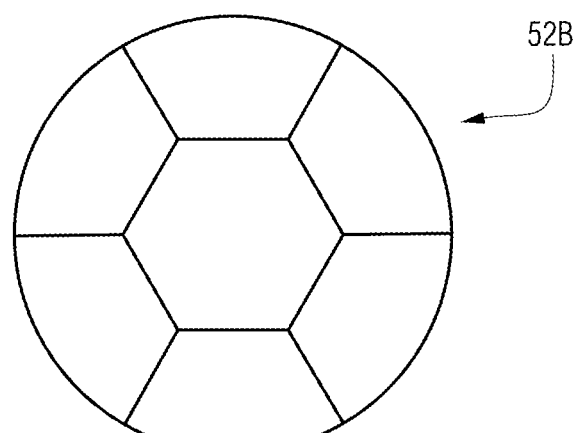

FIG. 4T is a schematic view of an inlet tube array for an RPT device in accordance with one form of the present technology.

Figure 4U:
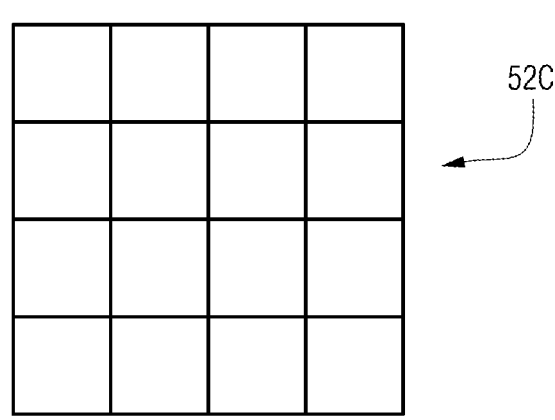

FIG. 4U is a schematic view of an inlet tube array for an RPT device in accordance with one form of the present technology.

Figure 4V:
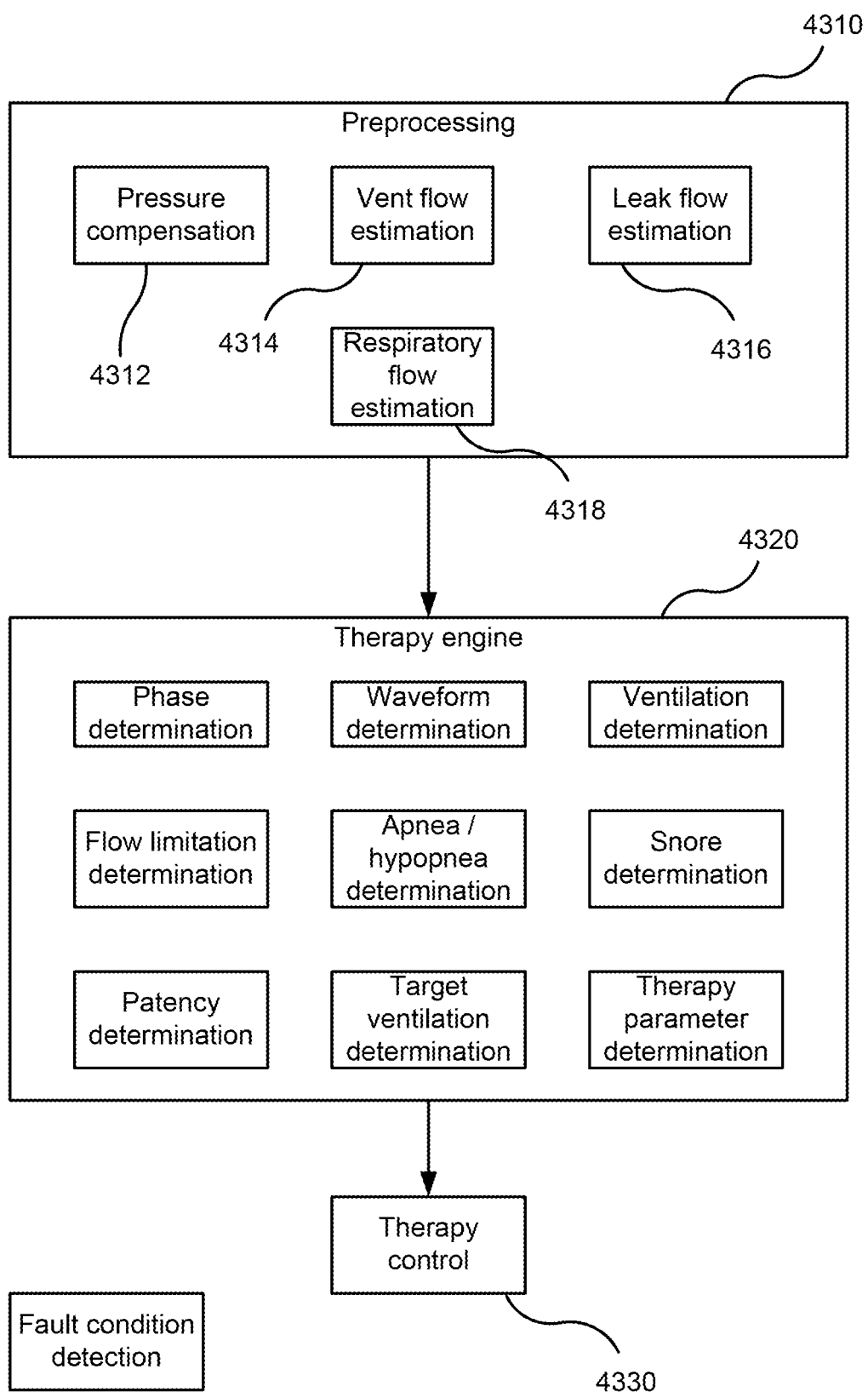

FIG. 4V is a schematic diagram of the algorithms implemented in an RPT device in accordance with one form of the present technology.

Figure 1A:
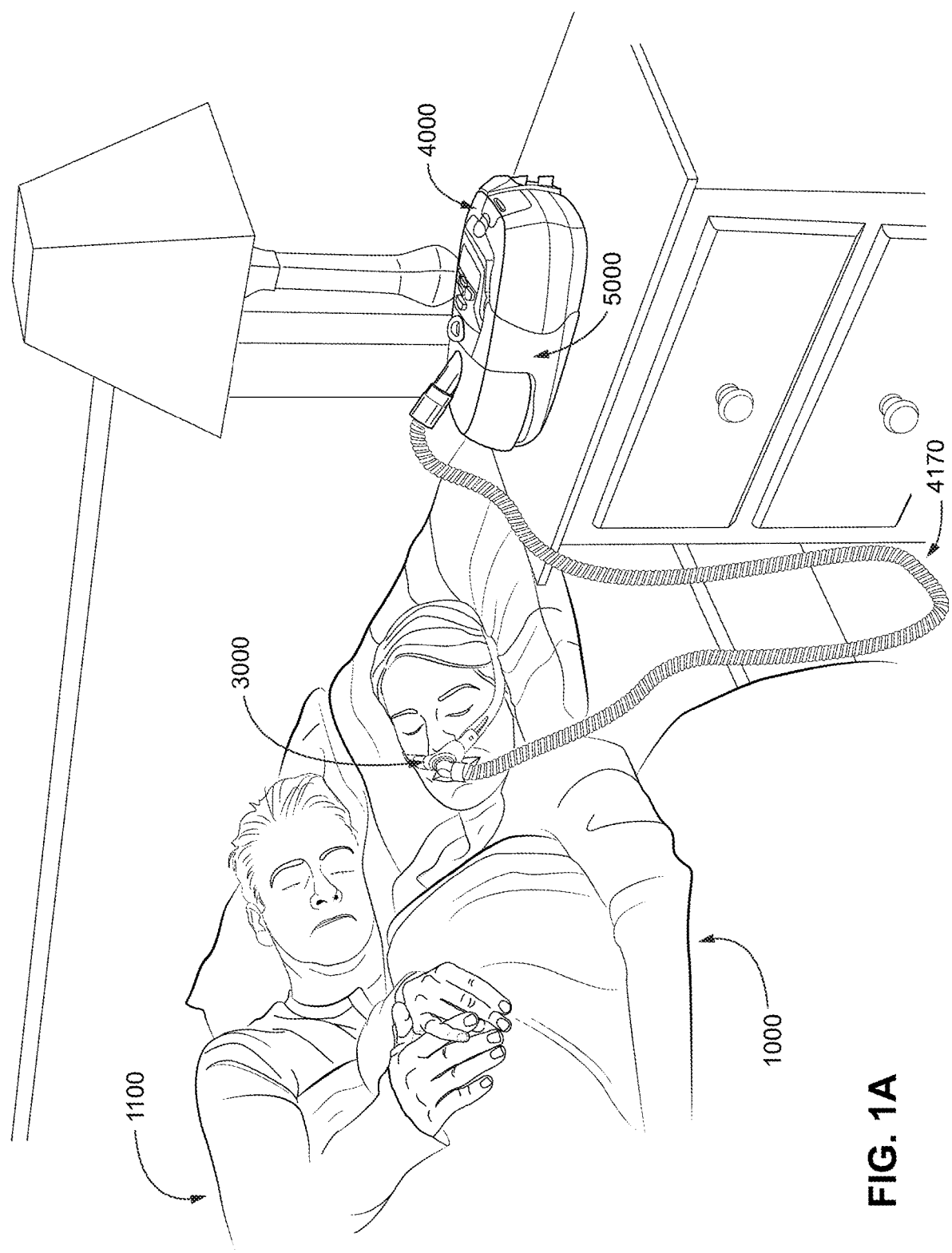
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
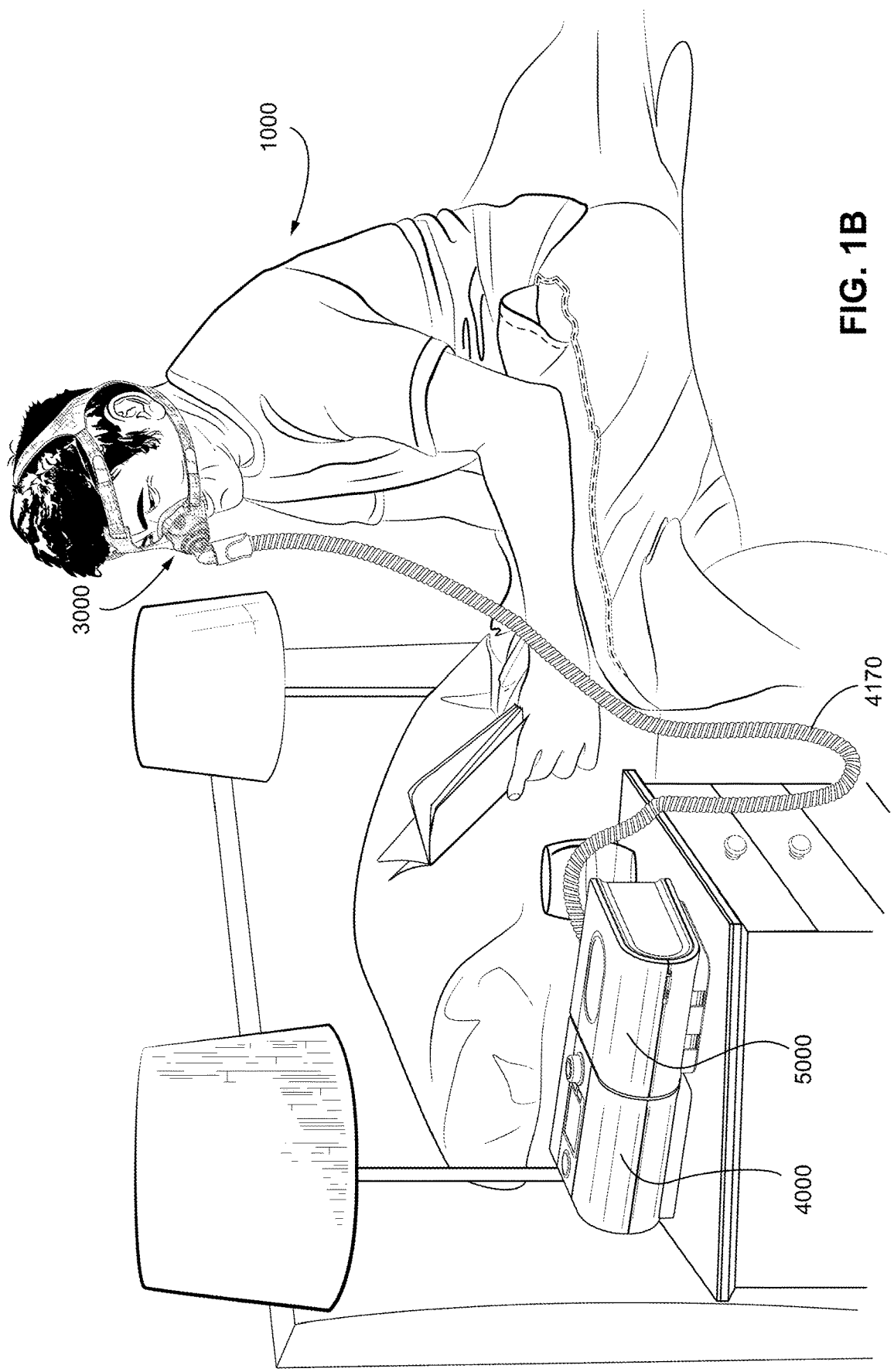
Figure 1C:

FIG. 4W1 is a perspective view of an external battery for powering an RPT device in accordance with one form of the present technology.

FIG. 4W2 is another perspective view of the external battery shown in FIG. 4W1.

FIG. 4X1 is a perspective view of the external battery of FIG. 4W1 being engaged with the RPT device of FIG. 4A in accordance with one form of the present technology.

FIG. 4X2 is another perspective view of the external battery and RPT device shown in FIG. 4X1.

FIG. 4Y1 is a perspective view of the external battery of FIG. 4W1 engaged with the RPT device of FIG. 4A in accordance with one form of the present technology.

FIG. 4Y2 is another perspective view of the external battery and RPT device shown in FIG. 4Y1.

FIG. 4Z1 is a perspective view of a blower and electrical connector in accordance with one form of the present technology.

FIG. 4Z2 is a perspective view of part of an RPT device including the blower and electrical connector shown in FIG. 4Z1.

4.5 Humidifier

Figure 5A:
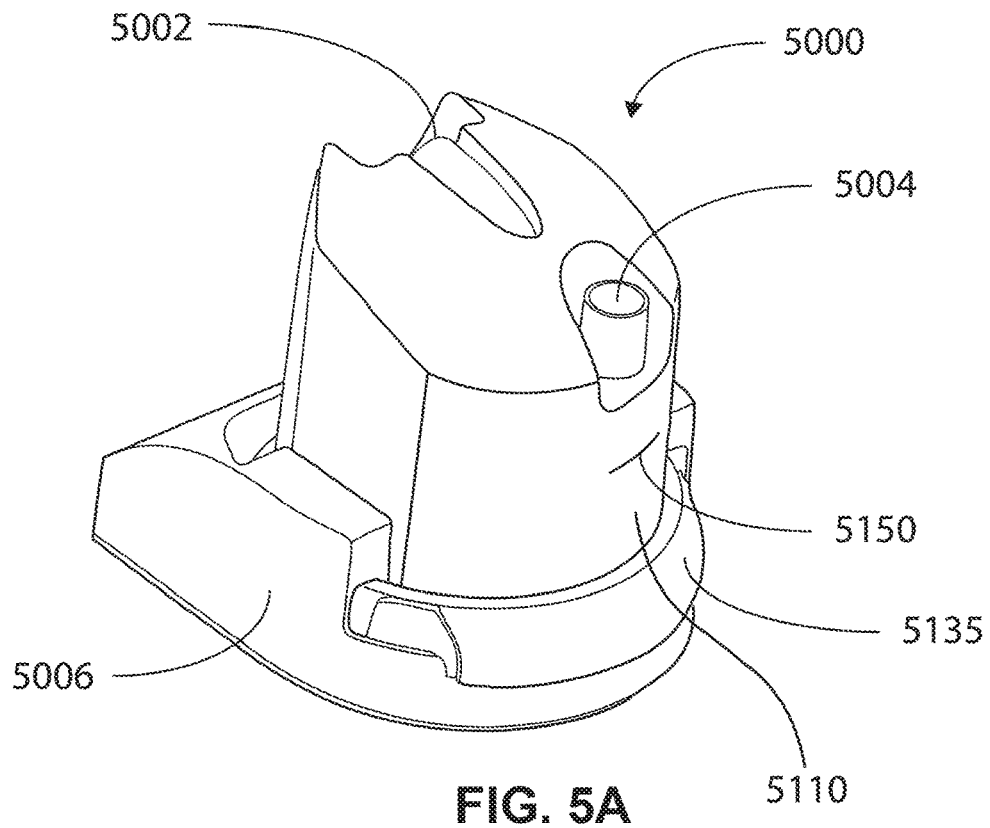

FIG. 5A shows an isometric view of a humidifier in accordance with one form of the present technology.

Figure 5B:
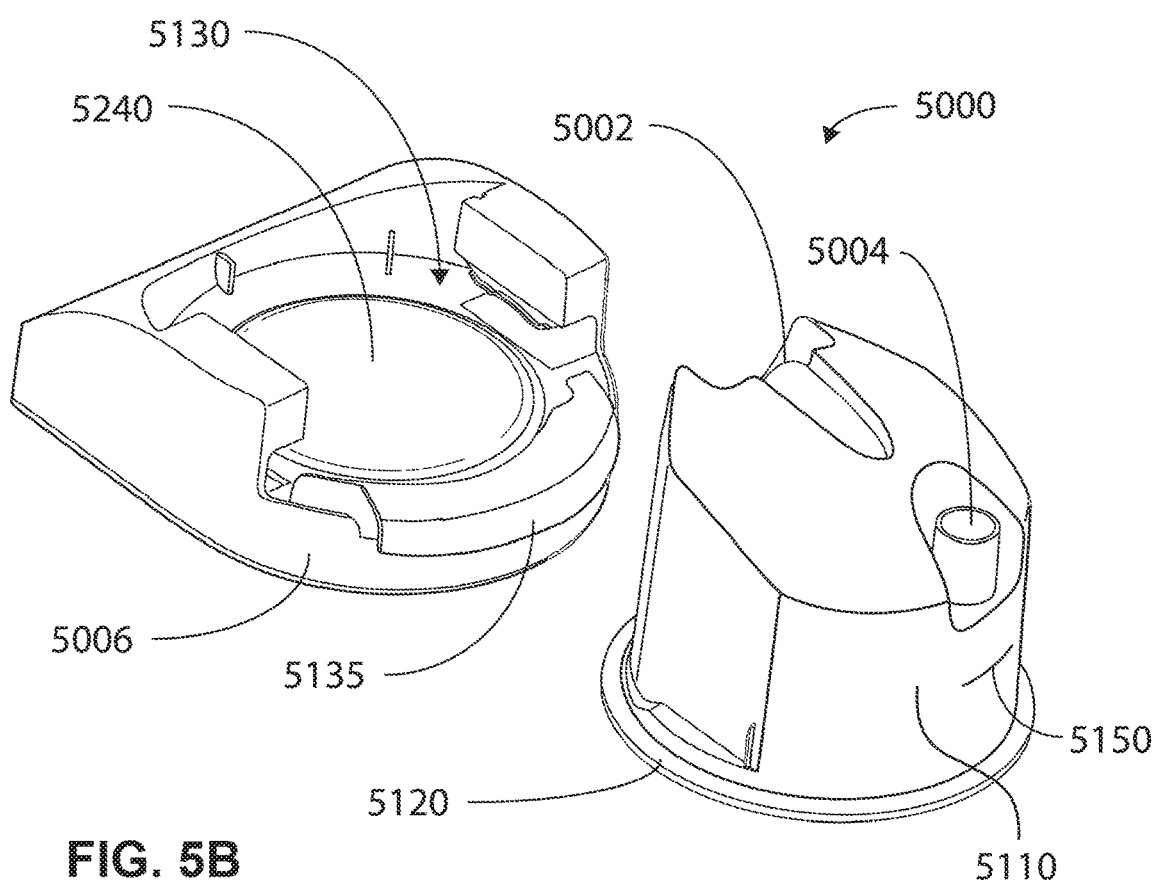

FIG. 5B shows an isometric view of a humidifier in accordance with one form of the present technology, showing a humidifier reservoir 5110 removed from the humidifier reservoir dock 5130.

Figure 5C:
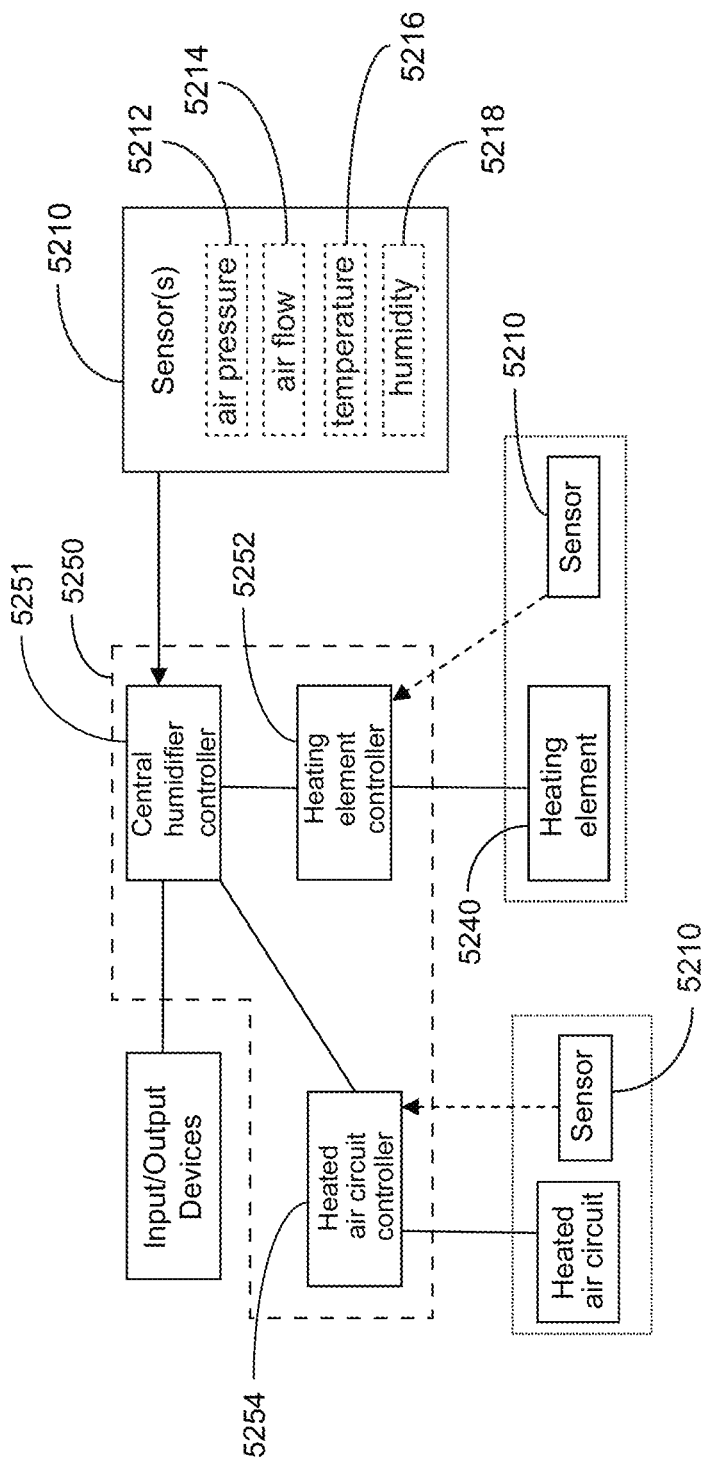

FIG. 5C shows a schematic of a humidifier in accordance with one form of the present technology.

4.6 Breathing Waveforms

Figure 6:
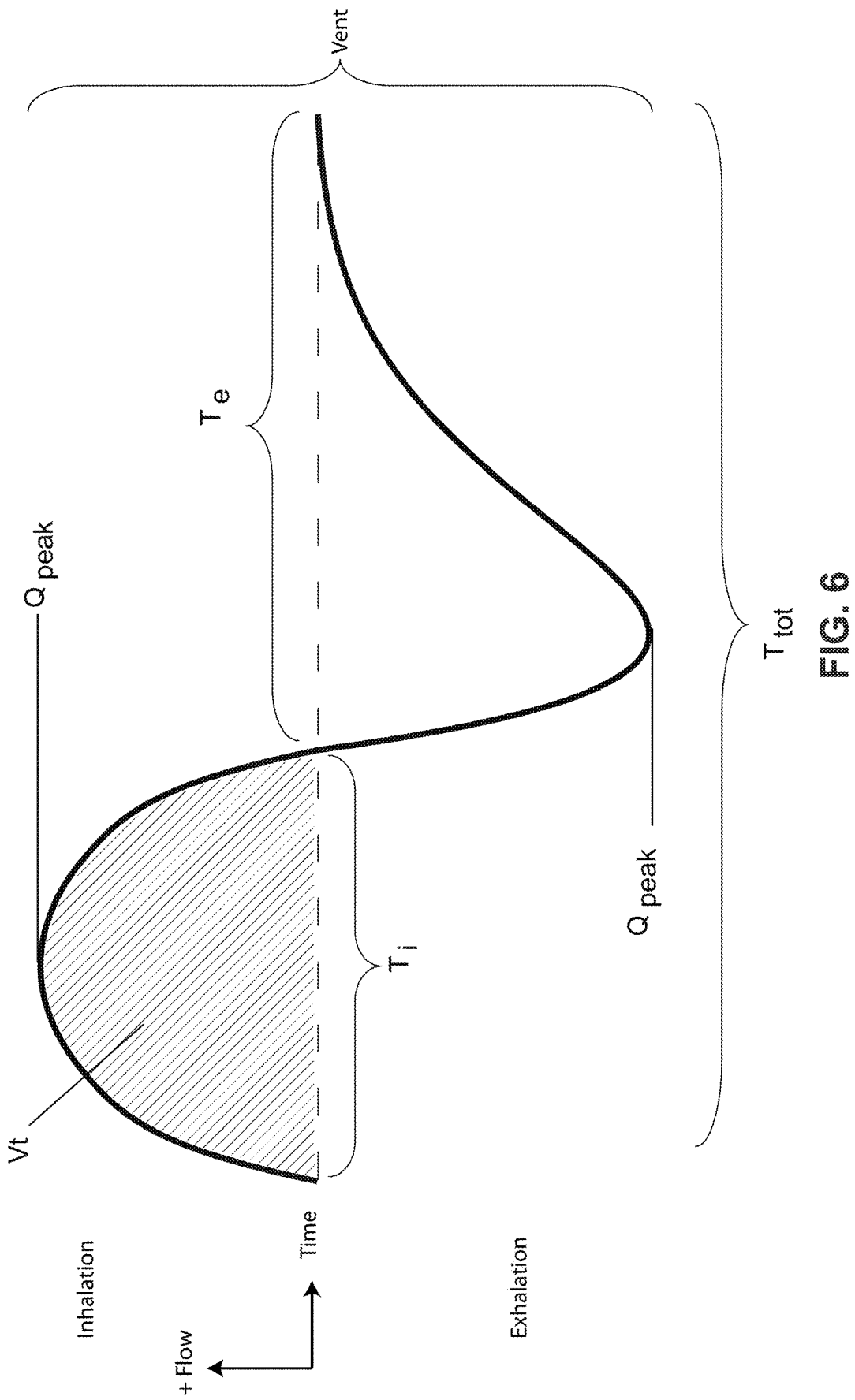

FIG. 6 shows a model typical breath waveform of a person while sleeping.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 or 8000 for supplying pressurised air to the patient 1000 via an air circuit 4170 to a patient interface 3000.

5.3 Patient Interface

As shown in FIG. 3, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

5.3.3 Positioning and Stabilising Structure

The seal-forming structure 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

5.3.4 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device in accordance with one aspect of the present technology comprises mechanical and pneumatic components, electrical components and is configured to execute one or more algorithms FIGS. 4A to 4R illustrate an RPT device 8000 according to an example of the present technology. As illustrated, the RPT device 8000 includes an external housing 8010 including an upper or top housing portion 8012, a lower or bottom housing portion 8014, a first end portion 8016 including a housing inlet 8018 and a housing outlet 8020, and a second end portion 8022 providing an end cover including faceplate 8024.

The housing 8010 supports and/or surrounds internal components of the RPT device 8000 including blower 8030, intermediate cover 8040, first plate assembly 8050, second plate assembly 8060, and a printed circuit board assembly (PCBA) 8070 including a main printed circuit board (main PCB) 8072 and a secondary printed circuit board (secondary PCB) 8074.

The housing 8010 and internal components of the RPT device 8000 cooperate to form the pneumatic air flow path or pneumatic block that extends from the housing inlet 8018 to the blower inlet 8032 of the blower 8030 and from the blower outlet 8034 of the blower 8030 to the housing outlet 8020.

In an example, the housing and the internal components cooperate to form an air flow path having a general U-shape extending from the housing inlet to the housing outlet. For example, the U-shaped air flow path may include an inlet leg extending from the housing inlet, an outlet leg extending from the housing outlet, and a connecting leg that interconnects the inlet leg and the outlet leg. In an example, the inlet leg and the outlet leg are generally parallel to one another. In an example, the blower is provided along a leg of the U-shape, e.g., along an outlet leg of the U-shape extending from the housing outlet. In an example, the blower includes an axis that is generally co-linear with an axis of the outlet leg of the U-shape. In an example, the U-shaped air flow path extends substantially in the same plane.

The RPT device 8000 is configured and structured to reduce noise output of the RPT device 8000 while maintaining a relatively small size.

In the illustrated example, the RPT device 8000 provides two chambers, i.e., first chamber 8001 and second chamber 8002. The first chamber 8001 is relatively large compared to the second chamber 8002. As illustrated, the blower 8030 is supported in the first chamber 8001, and receives air at the blower inlet 8032 from the second chamber 8002 (i.e., blower and blower inlet thereof located downstream of the chambers). The first and second plate assemblies 8050, 8060 define at least a portion of the first and second chambers 8001, 8002, and each of the first and second plate assemblies 8050, 8060 include a blower suspension 8054, 8064 that supports the blower 8030 within the first chamber 8001 and separates and seals air flow through the first chamber 8001 from air flow through an interior of the blower 8030. In addition, each of the first and second plate assemblies 8050, 8060 include at least one tube (e.g., inlet tube array 8052 and flow tube array 8062, respectively) such that air enters and exits the first chamber 8001 via at least one tube to reduce noise.

In the illustrated example best shown in FIG. 4E, the air flow path of the RPT device 8000 is structured and arranged such that air enters the housing 8010 via the housing inlet 8018, passes through the inlet tube array 8052 provided by the first plate assembly 8050, and into the first chamber 8001. The first chamber 8001 receives air from the inlet tube array 8052 and delivers the air to the flow tube array 8062 provided to the second plate assembly 8060. The air passes through the flow tube array 8062 and into the second chamber 8002. The second chamber 8002 receives air from the flow tube array 8062 and delivers the air to the blower inlet 8032 of the blower 8030. The air flows through the blower 8030 such that a flow of air at positive pressure is provided at the blower outlet 8034 of the blower 8030, which pressurized air exits the housing 8010 via the housing outlet 8020. The direction of air flow through inlet tube array 8052, first chamber 8001 and flow tube array 8062 is generally in a first direction, that direction being parallel to longitudinal axes of the inlet tubes 8055 and flow tubes 8065. The direction of air flow through blower 8030 is generally in a second direction, that direction being along the longitudinal axis of the blower 8030. The first and second directions are parallel and offset from each other by a lateral distance. The air flow through RPT device 8000 therefore follows a generally U-shaped or 'squared-U-shaped' path. This has the advantage of allowing a compact design of the RPT device.

In an example, one or more flow rate sensors may be provided to the RPT device 8000 and structured and configured to measure a first pressure in the first chamber 8001 and a second pressure in the second chamber 8002 to determine an air flow rate. The first pressure and the second pressure may be used to determine a flow rate based on a configuration of the flow tube array 8062, such as a pressure drop and/or the aerodynamic impedance. One flow rate sensor may be provided that is able to measure both the first and second pressures. Alternatively, two flow rate sensors may be provided: a first flow rate sensor to measure the first pressure in the first chamber 8001; and a second flow rate sensor to measure the second pressure in the second chamber 8002.

In an alternative example, one or more pressure sensors may be provided to the RPT device 8000 and may be structured and configured to measure a first pressure in the first chamber 8001 and a second pressure in the second chamber 8002 to determine an air flow rate. The pressure sensors may be in communication with a processor that is configured to determine the flow rate through the RPT device 8000 based on the received first and second pressure measurements. The processor may be located proximate to or remote from the pressure sensors, for example the pressure sensors and processor may be in wired or wireless communication.

5.4.1 RPT Device Mechanical & Pneumatic Components

An RPT device may comprise one or more of the following components in an integral unit. In an alternative form, one or more of the following components may be located as respective separate units.

5.4.1.1 Housing

As best shown in FIGS. 4H to 4K, the top housing portion 8012 of the housing 8010 includes a first part or base mold 8012A constructed of a relatively rigid material (e.g., polypropylene) and a second part or overmold 8012B constructed of a relatively soft material (e.g., thermoplastic elastomer (TPE) or silicone) that is provided (e.g., by overmolding) to the first part 8012A. In the illustrated example, the overmold 8012B is provided to an exterior surface of the base mold 8012A, however, it should be appreciated that the overmold 8012B may be provided to interior and/or exterior surfaces of the base mold 8012A. Softness of the overmold 8012B may provide a desirable tactile quality to a user of the RPT device 8000. The overmold 8012B may comprise a highly damped material to improve shock resistance and provide damping properties to attenuate wall-radiated noise.

As best shown in FIGS. 4A, 4B, 4H, 4J, and 4K, the top housing portion 8012 includes an on/off or power button 8003 and a wireless (e.g., Bluetooth) connection button 8004, each of which is structured and configured to interact with the PCBA 8070. However, it should be appreciate that the RPT device 8000 may include additional and/or alternative input devices to allow a user to interact with the device, e.g., one or more buttons, switches, dials, touch screen.

In the illustrated example, as best shown in FIGS. 4H, 4J, and 4K, the base mold 8012A provides a cantilevered button portion 8003A of the power button 8003 with a groove around the side of the button portion 8003A that allows the button portion 8003A to flex with respect to the base mold 8012A. The overmold 8012B provides a button portion 8003B including a raised portion of the power button 8003 and webbing within the groove around the side of the button portion 8003A. The raised portion and webbing of the button portion 8003B provide a soft tactile feel for ease of use and grip and spring (button return) force. Alternatively, the base mould 8012A may comprise an opening in the place of cantilevered button portion 8003A through which button portion 8003B in overmold 8012B can flex. With respect to the wireless (Bluetooth) connection button 8004, the base mold 8012A provides an opening 8004A and the overmold 8012B provides a button portion 8004B for a soft tactile feel for ease of use and grip and spring (button return) force.

The bottom housing portion 8014 of the housing 8010 includes a first part or base mold 8014A constructed of a relatively rigid material (e.g., polypropylene) and a second part or overmold 8014B constructed of a relatively soft material (e.g., TPE or silicone) that is provided (e.g., by overmolding) to the first part 8014A. In the illustrated example, the overmold 8014B is provided to an exterior surface of the base mold 8014A, however, it should be appreciated that the overmold 8014B may be provided to interior and/or exterior surfaces of the base mold 8014A. Softness of the overmold 8012B may provide a desirable tactile quality to a user of the RPT device 8000. The overmold 8014B may comprise a highly damped material to improve shock resistance and provide damping properties to attenuate wall-radiated noise.

As best shown in FIGS. 4F, 4G, and 4L, the bottom housing portion 8014 includes interior slots 8015A (e.g., formed by spaced apart side walls) along one end thereof structured and configured to receive and support the first plate assembly 8050 and interior slots 8015B (e.g., formed by spaced apart side walls) along an opposing end thereof structured and configured to receive and support the second plate assembly 8060. In the embodiment shown in FIGS. 4F, 4G, and 4L, slots 8015A and 8015B are provided in a plurality of slot sections separated by gaps. In an alternative embodiment of the invention, slots 8015A and/or 8015B span across the width of bottom housing portion 8014, e.g. additional slot sections are provided which span the gaps between the slot sections shown in FIGS. 4F, 4G, and 4L.

Interior blower supports, such as interior ribs 8017, constructed of a relatively soft, high damping material (e.g., TPE or silicone) are provided (e.g., by overmolding) to the bottom housing portion 8014, e.g., see FIGS. 4F and 4I. The interior ribs 8017 are axially spaced between the slots 8015A, 8015B and are structured and configured to at least partially surround the blower 8030 to provide support, shock resistance and/or damping properties for the blower 8030. One or more additional interior blower supports, such as additional ribs may be provided to the housing at alternative locations, e.g., to provide shock resistance and/or damping properties. It is contemplated that interior blower supports may be in alternative forms, for example as bumps or plates.

The housing 8010 of the RPT device 8000 may comprise a guiding member to facilitate alignment and connection of the RPT device 8000 with one or more complementary components of a respiratory treatment system, such as a humidifier 5000 and/or an external battery 9000 for powering the RPT device 8000. For example, the bottom housing portion 8014 includes a rail 8019 on each side thereof. In an example, the rails 8019 may also facilitate alignment and connection of the top and bottom housing portions 8012, 8014 and/or facilitate handling/grip of the RPT device 8000.

Each rail 8019 may define or comprise a movement path for the RPT device 8000 in relation to the complementary component, such as in a form of an elongate rectangular indent as shown in FIG. 4H or an elongate, longitudinal protrusion as shown in FIG. 4X1. Other forms of course may be also suitable.

One or more of the rails 8019 may comprise a retention mechanism (e.g., a recessed slot 8110 as shown in FIGS. 4X1 and 4X2) for latching the RPT device 8000, which may also be used to disengage the RPT device from the complementary component connected thereto.

In some forms, each rail 8019 may be configured for relative movement against a complementary roller, bearing or a guide. It will be understood that alternatively, an RPT device 8000 may comprise a roller, bearing, or a guide for engagement to a rail located on a complementary component.

The top and bottom housing portions 8012, 8014 may be connected to one another in any suitable manner, e.g., mechanical fasteners, mechanical interlock and/or snap-fit connection.

The first end portion 8016 is supported by the top and bottom housing portions 8012, 8014, e.g., connected to the top and bottom housing portions 8012, 8014 by mechanical fasteners, mechanical interlock and/or snap-fit connection. The first end portion 8016 is supported adjacent the first plate assembly 8050 such that the housing inlet 8018 is structured and configured to communicate with the inlet tube array 8052 of the first plate assembly 8050 and the housing outlet 8020 is structured and configured to communicate with an outlet bellows 8056 of the first plate assembly 8050, as described in greater detail below.

The first end portion 8016 includes a cover plate 8021 with a plurality of openings 8023 that provide the housing inlet 8018. The plurality of openings 8023 allow sufficient airflow while preventing the ingress of larger objects. A recessed opening 8025 (e.g., see FIGS. 4F and 4G) is provided to the first end portion 8016 in communication with the plurality of openings 8023. The recessed opening 8025 interfaces with the inlet tube array 8052 provided to the first plate assembly 8050, such that air flows through the plurality of openings 8023 and the opening 8025 to the inlet tube array 8052 in communication with the first chamber 8001.

The housing outlet 8020 includes a tube portion 8026 structured and configured to receive and retain an end of the air circuit 4170, e.g., cuff of an air delivery tube. The tube portion 8026 and the end of the air circuit may be connected to one another in any suitable manner, e.g., mechanical interlock, snap-fit connection and/or friction-fit. The interior of the tube portion 8026 is structured and configured to communicate with the outlet bellows 8056 of the first plate assembly 8050, which allows the end of the air circuit 4170 to engage and form a seal with the outlet bellows 8056 which is in communication with the blower outlet 8034 of the blower 8030, thereby forming a seal for the air path. Further examples and details of the connection of the air circuit to an outlet of an RPT device are disclosed in U.S. Provisional Appln. No. 62/130,813, filed Mar. 10, 2015, which is incorporated herein by reference in its entirety.

The first end portion 8016 also includes an opening or tube portion 8027 structured and configured to receive and retain an end of an electrical plug. The tube portion 8027 and the end of the electrical plug may be connected to one another in any suitable manner, e.g., mechanical interlock, snap-fit connection and/or friction-fit. The interior of the tube portion 8027 is structured and configured to communicate with an electrical socket 8080, which allows the end of the electrical plug to electrically engage with the electrical socket 8080, thereby allowing electrical power to be supplied to the RPT device 8000.

The second end portion 8022 is supported by the top and bottom housing portions 8012, 8014, e.g., connected to the top and bottom housing portions 8012, 8014 by mechanical fasteners, mechanical interlock and/or snap-fit connection. The second end portion 8022 cooperates with an interior wall 8028 (i.e., provided by the bottom housing portion 8014 and the intermediate cover 8040) to define an interior chamber portion 8006 (e.g., see FIG. 4I) structured and configured to receive the secondary PCB 8074. The interior chamber portion 8006 is exterior the air path.

5.4.1.2 Blower

In the illustrated example, the blower 8030 of the RPT device 8000 includes a three-stage design structured and configured for producing a flow, or a supply, of air at positive pressure up to 45-50 cmH$_2$O, e.g., in the range of 2-50 cmH$_2$O, e.g., 3-45 cmH$_2$O, 4-30 cmH$_2$O. However, in alternative examples, the blower 8030 may include a single stage design, a two stage design, or four or more stage designs.

As best shown in FIG. 4I, the blower 8030 includes a housing 8031 including an axial air inlet (blower inlet) 8032 and axial air outlet (blower outlet) 8034 between which are located three stages with three corresponding impellers 8033A, 8033B, 8033C, i.e., first and second impellers 8033A, 8033B positioned on one side of the motor 8035 and a third impeller 8033C positioned on the other side of the motor 8035. However, other suitable impeller arrangements are possible. Each impeller is followed by a set of stator vanes structured and configured to direct the air flow to the next stage.

In the illustrated example, the blower 8030 is supported within the first chamber 8001 and the blower housing 8031 is relatively rigid and structured and configured to sealingly separate air flow through an interior of the blower 8030 from the first chamber 8001. In an example, the housing 8031 may comprise a plurality of housing portions (e.g., first housing part including inlet 8032, second housing part including outlet 8034, and intermediate housing parts (e.g., stationary components providing stator vanes to direct air flow) that are connected to one another (e.g., welded) to a form a substantially sealed structure.

Further examples and details of the blower 8030 are described in PCT Patent Application Publication No. WO 2013/020167, which is incorporated herein by reference in its entirety.

As described in greater detail below, the first plate assembly 8050 and the second plate assembly 8060 each include a blower suspension 8054, 8064 that cooperate to support the blower 8030 within the housing 8010, provide seals for the air path, isolate vibrations of the blower, and provide shock resistance. The blower suspension 8054, 8064 may provide additional spring and damping to isolate vibrations and provide shock resistance. For example, blower suspension 8054, 8064 may be formed from a flexible material such as an elastomer. Specifically, the first plate assembly 8050 provides an outlet end suspension 8054 to support the blower 8030 adjacent the blower outlet 8034 and the second plate assembly 8060 provides an inlet end suspension 8064 to support the blower 8030 adjacent the blower inlet 8032, i.e., a suspension is located at each end of the blower 8030.

The blower 8030 may be mounted within housing 8010 so that the blower suspension 8054, 8064 is in a neutral state or, alternatively the blower 8030 may be mounted so that the blower suspension 8054, 8064 is in tension. For example, slots 8015A and 8015B in bottom housing portion 8014 may be located so that the slots are further apart than the distance between first plate assembly 8050 and second plate assembly 8060 when the blower suspension 8054, 8064 is in its neutral state and the plate assemblies 8050 and 8060 are not mounted in slots 8015A and 8015B, for example the RPT device 8000 is in an unassembled state. In assembling blower 8000 in this way, the first and second plate assemblies 8050 and 8060 are pulled apart in order to insert the first and second plate assemblies 8050, 8060 into the respective slots 8015A, 8015B in the bottom housing portion 8014, which stretches blower suspension 8054, 8064. This may assist in isolating vibrations in the blower 8030, for example by reducing sag in the blower suspension 8054, 8064 and reducing the possibility of the blower 8030 contacting the internal surfaces of the interior ribs 8017 during use.

5.4.1.3 Intermediate Cover

The intermediate cover 8040 (also referred to as an intermediate housing portion of the housing) is supported between the top and bottom housing portions 8012, 8014 of the housing 8010. The intermediate cover 8040 is structured and configured to define at least a portion of the air path (e.g., define top and sides of the air path) and to define at least a portion of interior chamber portions exterior of the air path to receive the PCBA 8070.

Similar to the bottom housing portion 8014 described above, the intermediate cover 8040 includes interior slots 8042A (e.g., formed by spaced apart side walls) along one end thereof structured and configured to receive and support the first plate assembly 8050 and interior slots 8042B (e.g., formed by spaced apart side walls) along an opposing end thereof structured and configured to receive and support the second plate assembly 8060, e.g., see FIGS. 4H and 4L. Accordingly, the intermediate cover 8040 cooperates with the bottom housing portion 8014 to support and retain the first and second plate assemblies 8050, 8060 within the RPT device 8000.

In the illustrated example, the intermediate cover 8040 may constitute an upper portion and the bottom housing portion 8014 may constitute a lower portion, the upper and lower portions being engageable or separable in a generally normal direction with respect an axis of the inlet tubes 8055/flow tubes 8065 of each of the first and second plate assemblies 8050, 8060 and/or in a direction generally in plane or parallel with respect to the base plate 8051, 8061. In an example, the upper and lower portions are engageable or separable in a generally normal direction with respect an axis of at least one tube of the first plate assembly 8050.

The intermediate cover 8040 also includes an end wall 8028A that cooperates with an end wall 8028B of the bottom housing portion 8014 to define interior wall 8028, e.g., see FIGS. 4I and 4L. Interior wall 8028 separates the air flow path from the interior chamber portion 8006 configured to receive the secondary PCB 8074, e.g., see FIG. 4I. Also, the main wall 8044 of the intermediate cover 8040 cooperates with the top housing portion 8012 to define an interior chamber portion 8007 to receive the main PCB 8072, e.g., see FIG. 4I. Accordingly, the intermediate cover 8040 defines interior chamber portions 8006, 8007 exterior of the air path to receive the main and secondary PCBs 8072, 8074.

The intermediate cover 8040, along with the bottom housing portion 8014 and the first and second plate assemblies 8050, 8060, cooperate to define the top, bottom, and sides of the first and second chambers 8001, 8002, and therefore the pneumatic air path that extends to the blower inlet 8032 of the blower 8030.

In the illustrated example, the intermediate cover 8040 includes a first part or base mold 8040A constructed of a relatively rigid material (e.g., polypropylene) and a second part or overmold 8040B constructed of a relatively soft material (e.g., TPE or silicone) that is provided (e.g., by overmolding) to the first part 8040A. In the illustrated example, the overmold 8040B is provided to an interior surface of the base mold 8040A, i.e., overmold 8040B provided along the air flow path. The overmold 8040B provides damping properties to attenuate wall-radiated noise. However, it should be appreciated that the overmold 8040B may be provided to interior and/or exterior surfaces of the base mold 8040A.

Also, the overmold 8040B extends along the edges of the intermediate cover 8040, which cooperates with sealing (e.g., TPE or silicone) provided along side wall edges of the bottom housing portion 8014, to seal the air path.

5.4.1.4 First Plate Assembly

As best shown in FIGS. 4M, 4N, and 4I, the first plate assembly 8050 includes a base plate 8051, an inlet tube array 8052, and a tube portion 8053 including a blower suspension (outlet end suspension) 8054 along one end and an outlet bellows 8056 along the opposite end. The tube portion 8053 includes an opening 8053A (e.g., see FIG. 4N) communicated with a pressure port 8058. In addition, a sealing lip or sealing flange 8059 is provided along the edge or perimeter of the base plate 8051.

In an example, the base plate 8051, the inlet tube array 8052, and the tube portion 8053 comprise a first part or base mold constructed of a relatively rigid material (e.g., polypropylene), and the blower suspension 8054, outlet bellows 8056, pressure port 8058, and sealing lip 8059 comprise a second part or overmold constructed of a relatively soft material (e.g., TPE or silicone) that is provided (e.g., by overmolding) to the first part.

As described above, the first plate assembly 8050 is supported between the intermediate cover 8040 and the bottom housing portion 8014, i.e., base plate 8051 supported within interior slots 8042A, 8015A provided by the intermediate cover 8040 and the bottom housing portion 8014. The base plate 8051 defines a wall of the first chamber 8001 and the sealing lip 8059 along the perimeter of the base plate 8051 provides a seal along the edge of the first chamber 8001.

The blower suspension 8054 of the first plate assembly 8050 is in the form of an outlet end suspension to support the blower 8030 adjacent the blower outlet 8034 of the blower 8030. The outlet end suspension 8054 (e.g., constructed of an elastomeric material such as TPE or silicone) includes a first end portion 8054A provided (e.g., overmolded) to the tube portion 8053, a second end portion 8054B engaged or otherwise secured to the blower outlet 8034 of the blower 8030, and a radially outwardly extending gusset portion 8054C between the first and second end portions 8054A, 8054B.

The second end portion 8054B may be secured to the blower 8030 in any suitable manner, e.g., wrap around an outlet flange provided to blower outlet 8034 as shown in FIG. 4I. The blower suspension 8054 seals the blower outlet 8034 to the tube portion 8053, thereby sealing the air path for air exiting the blower outlet 8034 from the first chamber 8001. Also, the gusset portion 8054C of the blower suspension 8054 allows flexibility and relative movement to isolate vibrations of the blower 8030 and provide shock resistance.

As described above, the outlet bellows 8056 of the first plate assembly 8050 is provided within the tube portion 8026 of the housing outlet 8020, and is structured and configured to form a seal with an end of the air circuit 4170, e.g., cuff of an air delivery tube. The outlet bellows 8056 (e.g., constructed of an elastomeric material such as TPE or silicone) includes an end portion 8056A provided (e.g., overmolded) to the tube portion 8053 and a bellows portion 8056B that curves radially inwardly from the end portion 8056A. The bellows portion 8056B is flexible to allow the end of the air circuit to engage and form a seal with the bellows portion 8056B. As shown in FIG. 4M, the perimeter of the outlet bellows 8056B may be provided with spaced part projections 8056C, e.g., to add rigidity to the base of the outlet bellows 8056B.

The pressure port 8058, which may be integral with the blower suspension 8054, is structured and configured to interface or otherwise connect to a pressure sensor.

The inlet tube array 8052 includes a plurality of inlet tubes 8055 structured and configured to extend from the base plate 8051 into the first chamber 8001, e.g., inlet tubes 8055 extend generally perpendicular with respect to the base plate 8051. In the illustrated example, the inlet tube array 8052 provides a first end portion 8052A that slightly protrudes from one side of the base plate 8051 so as to interface with the recessed opening 8025 in the first end portion 8016 of the housing 8010. As illustrated, the recessed opening 8025 includes shape that corresponds to a shape of the first end portion 8052A along its outer perimeter. The second end portion 8052B of the inlet tube array 8052 protrudes from the other side of the base plate 8051 so as to extend into the first chamber 8001. Thus, the air flow path extends from the housing inlet 8018, through the inlet tube array 8052, and into the first chamber 8001.

This arrangement reduces noise output of the RPT device 8000 by increasing acoustic impedance through the inlet tubes 8055 while maintaining a high inertance. In an example, longer inlet tubes 8055 may be preferable for noise reduction (due to the higher inertance), and the length of the inlet tubes 8055 may be tuned or selected to match the specific noise frequency characteristics of the RPT device 8000.

In an example, the length of inlet tubes 8055 may be configured such that it does not adversely interact with any high-amplitude noise frequencies. For example, the length of inlet tubes 8055 may be tuned such that it does not coincide with ¼ or ½ wavelengths of any peaks in the blower's noise spectrum. Peaks in the blower's noise spectrum (i.e., tonal peaks) may be caused by one or more of bearing defects, blade pass, turbulence, and structural resonance.

In the illustrated example, each of the plurality of inlet tubes 8055 includes a non-circular cross-sectional shape (e.g., hexagonal cross-sectional shape), and the plurality of inlet tubes 8055 are arranged adjacent to one another to form the inlet tube array 8052. That is, the inlet tubes 8055 are arranged adjacent to one another such that adjacent tubes share at least one side wall or side wall portion, i.e., adjacent tubes include at least one common side wall or side wall portion. As illustrated, adjacent tubes 8055 are separated by a thin wall to allow efficient packaging of the inlet tube array 8052. The use of a plurality of relatively small inlet tubes 8055 may also further encourage the flow travelling therethrough to be laminar.

In an example, each of the plurality of inlet tubes 8055 may comprise a draft angle to allow a mould tool to be extracted from the tubes during the moulding process. Such draft angle may be in either direction, i.e., converging away from the base plate 8051 or towards the base plate 8051.

In an example, each of the plurality of inlet tubes 8055 includes a length of about 35-55 mm (e.g., about 40-50 mm, e.g., about 43 mm), a wall thickness of about 1 mm, and a flat-to-flat distance (diameter) of about 3-5 mm (e.g., about 3.5-4.5 mm, e.g., about 4.33 mm). Thus the cross-sectional area of each hexagonal tube 8055 may be about 10-20 mm$^2$ (e.g., about 16.2 mm$^2$), and the total cross-sectional area of all inlet tubes 8055 may be about 100-130 mm$^2$ (e.g., about 110-120 mm$^2$, e.g., about 114 mm$^2$). However, it should be appreciated that other suitable lengths, wall thicknesses, flat-to-flat distances (diameters), and cross-sectional areas of the tubes 8055 are possible, e.g., depending on the desired noise characteristic.

In the illustrated example, the inlet tube array 8052 includes seven inlet tubes 8055 arranged with six inlet tubes about a central inlet tube. However, it should be appreciated that other suitable number of tubes 8055 are possible (e.g., one or more inlet tubes, e.g., 5-10 inlet tubes) and the tubes 8055 may be arranged in other suitable manners (e.g., spaced apart, aligned in columns, etc.)

Each of the plurality of inlet tubes 8055 may be constructed as a single part, or may comprise multiple parts. For example, each inlet tube 8055 may comprise an outer tube and an inlet restrictor configured to change a diameter of the tube.

The plurality of inlet tubes 8055 may comprise inlet tubes of equal lengths and/or unequal lengths. The plurality of inlet tubes 8055 may comprise a sloped shape at one or more ends.

Also, each of the plurality of inlet tubes 8055 may include other cross-sectional shapes, e.g., circular shape or noncircular shape (e.g., square, rectangle). In the illustrated example, the inlet tube array 8052 includes an outer perimeter with a non-circular shape. However, the outer perimeter shape of the inlet tube array 8052 may include other suitable shapes, e.g., circular shape or noncircular shape.

For example, FIGS. 4S to 4U illustrate alternative arrangements for the inlet tube array 8052. In FIG. 4S, the inlet tube array 52A includes a circular outer perimeter with each inlet tube including a square or truncated-square shape. In FIG. 4T, the inlet tube array 52B includes a circular outer perimeter with each inlet tube including a hexagon or truncated-hexagon shape. In FIG. 4U, the inlet tube array 52C includes a square outer perimeter with each inlet tube including a square shape.

5.4.1.5 Second Plate Assembly

As best shown in FIGS. 4O and 4P, the second plate assembly 8060 includes a base plate 8061, a flow tube array 8062, and a blower suspension (outlet end suspension) 8064 supported within an opening 8063 provided to the base plate 8061. In addition, a sealing lip or sealing flange 8069 is provided along the edge or perimeter of the base plate 8061.

In an example, the base plate 8061 and the flow tube array 8062 comprise a first part or base mold constructed of a relatively rigid material (e.g., polypropylene), and the blower suspension 8064 and sealing lip 8069 comprise a second part or overmold constructed of a relatively soft material (e.g., TPE or silicone) that is provided (e.g., by overmolding) to the first part.

As described above, the second plate assembly 8060 is supported between the intermediate cover 8040 and the bottom housing portion 8014, i.e., base plate 8061 supported within interior slots 8042B, 8015B provided by the intermediate cover 8040 and the bottom housing portion 8014. The base plate 8061 defines a wall of the first chamber 8001 and the second chamber 8002, and the sealing lip 8069 along the perimeter of the base plate 8061 provides a seal along the edge of the first and second chambers 8001, 8002.

The blower suspension 8064 of the second plate assembly 8060 is in the form of an inlet end suspension to support the blower 8030 adjacent the blower inlet 8032 of the blower 8030. The inlet end suspension 8064 (e.g., constructed of an elastomeric material such as TPE or silicone) includes a radially outer portion 8064A provided (e.g., overmolded) to the opening 8063 of the base plate 8061, a radially inner portion 8064B engaged or otherwise secured to the blower inlet 8032 of the blower 8030, and an intermediate portion 8064C between the outer and inner portions 8064A, 8064B.

The radially inner portion 8064B may be secured to the blower 8030 in any suitable manner, e.g., wrap around an inlet flange provided to the blower inlet 8032 as shown in FIG. 4I. The blower suspension 8064 provides a seal along the blower inlet 8032, thereby sealing the blower inlet 8032 from the first chamber 8001 and providing an air path for air entering the blower inlet 8032 from the second chamber 8002. Also, in the illustrated example, the intermediate portion 8064C of the blower suspension 8064 is axially offset from the outer and inner portions 8064A, 8064B, which allows flexibility and relative movement to isolate vibrations of the blower 8030 and provide shock resistance.

The flow tube array 8062 includes a plurality of flow tubes 8065 structured and configured to extend from the base plate 8061 into the first chamber 8001, e.g., flow tubes 8065 extend generally perpendicular with respect to the base plate 8061. In the illustrated example, each flow tube 8065 includes a first end portion 8065A provided to the base plate 8061 and a second end portion 8065B that protrudes from the base plate 8061 so as to extend into the first chamber 8001. Thus, the air flow path extends from first chamber 8001, through the flow tube array 8062, and into the second chamber 8002.

Similar to the inlet tube array 8052, the flow tube array 8062 is configured and arranged to reduce noise output of the RPT device 8000 by increasing acoustic impedance through the flow tubes 8065 while maintaining a high inertance.

In the illustrated example, the flow tube array 8062 includes six, spaced-apart flow tubes 8065 generally arranged in three columns of two tubes with the columns generally offset from one another. However, it should be appreciated that other suitable number of tubes 8065 are possible (e.g., one or more flow tubes, e.g., 4-10 flow tubes) and the tubes 8065 may be arranged in other suitable manners (e.g., aligned in rows and/or columns, circular arrangement, adjacent tubes engaged with one another, etc.).

In the illustrated example, each of the plurality of flow tubes 8065 includes a circular cross-sectional shape, however it should be appreciated that each of the tubes 8065 may include other cross-sectional shapes, e.g., circular shape or noncircular shape.

In an example, each of the plurality of flow tubes 8065 may include any suitable length, diameter, wall thickness, and cross-sectional area, e.g., depending on the desired noise characteristic. In an example, the length of the flow tubes 8065 may be tuned or selected to match the specific noise frequency characteristics of the RPT device 8000.

In an example, each of the plurality of flow tubes 8065 may comprise a draft angle to allow a mould tool to be extracted from the tubes during the moulding process. Such draft angle may be in either direction, i.e., converging away from the base plate 8061 or towards the base plate 8061.

The plurality of flow tubes 8065 may comprise flow tubes of equal lengths and/or unequal lengths. The plurality of flow tubes 8065 may comprise a sloped shape at one or more ends.

5.4.1.6 Arrangement of Inlet Tube Array and Flow Tube Array

In the illustrated example, the inlet tube array 8052 and the flow tube array 8062 are structured and arranged with respect to one another within the first chamber 8001 to reduce noise output of the RPT device 8000.

As best shown in FIGS. 4Q and 4R, the inlet tube array 8052 is axially spaced from the flow tube array 8062, and the tubes 8055 of the inlet tube array 8052 include axes that are arranged substantially parallel to axes of the tubes 8065 of the flow tube array 8062, however the tubes 8055 of the inlet tube array 8052 are not arranged co-axially with the tubes 8065 of the flow tube array 8062. This arrangement reduces an amount of noise that is radiated through the flow tube array 8062 and then directly to the inlet tube array 8052.

The axially offset arrangement may be provided by off-setting a central axis of the inlet tube array 8052 (i.e., center axis defined by combination of all inlet tubes 8055) from a central axis of the flow tube array 8062 (i.e., center axis defined by combination of all flow tubes 8065) and/or the axially offset arrangement may be provided by arranging the inlet tube array 8052 and the flow tube array 8062 such that one or more of the individual tubes 8055, 8065 are not co-axial or axially aligned (i.e., axially offset) with one another. For example, FIG. 4R shows an arrangement wherein each of tubes 8055 of the inlet tube array 8052 includes an axis that is axially offset from axis of each of the tubes 8065 of the flow tube array 8062 (i.e. none of the tubes 8055 is co-axial with any of the tubes 8065).

In an in-line configuration as illustrated, the tubes 8055 of the inlet tube array 8052 may be axially spaced from the tubes 8065 of the flow tube array 8062, e.g., the spacing d (see FIG. 4Q) between the inlet tube array 8052 and the flow tube array 8062 may be at least 5 mm, e.g., between about 10-15 mm.

Also, in the illustrated example, the tubes 8055 of the inlet tube array 8052 and the tubes 8065 of the flow tube array 8062 each includes axes that are aligned substantially parallel with an axis of the blower 8030.

5.4.1.7 Printed Circuit Board Assembly

As described above, the PCBA 8070 includes a main PCB 8072 and a secondary PCB 8074, the main PCB 8072 supported within interior chamber portion 8007 (e.g., defined by the top housing portion 8012 and the intermediate cover 8040), and the secondary PCB 8074 supported within interior chamber portion 8006 (e.g., defined by the second end portion 8022, the intermediate cover 8040, and the bottom housing portion 8014). This arrangement positions the main PCB 8072 and the secondary PCB 8074 exterior of the air flow path.

The PCBA 8070 is electrically connected to the blower 8030 by one or more electrical connectors, e.g., electrical connector 8090 shown in FIGS. 4H and 4L. In the example shown in FIG. 4G, the blower 8030 includes an electrical connector portion 8038 extending exterior the blower housing 8031, and the electrical connector 8090 is structured and arranged to electrically connect the electrical connector portion 8038 of the blower 8030 to the PCBA 8070.

In an example, the electrical connector 8090 may be a flexible circuit board (FCB), flexible printed circuits (FPC) and/or flexible flat cables (FFC) to electrically connect the blower 8030 to the PCBA 8070.

In an example, the electrical connector 8090 may be arranged to pass through an internal air chamber (e.g., through the first chamber 8001) of the RPT device 8000, while not being positioned directly in the air flow path, e.g., such as between the inlet tube array 8052 and the flow tube array 8062. For example, in the illustrated example, the electrical connector 8090 may be arranged to pass around a periphery of the inlet tube array 8052.

The electrical connector 8090 may be pre-formed to a particular shape to reduce potential interference with one or more components of the RPT device 8000. Also, the electrical connector 8090 may be sufficiently long such that the electrical connector 8090 remains slack when connected, e.g., to isolate vibration from being transmitted from the blower 8030 through the electrical connector 8090.

In an example, the electrical connector 8090 may be structured and configured to help achieve a reliable seal due to its low-profile form factor. In an example, tape and/or adhesives may be used to further seal any gaps where the electrical connector 8090 exits housing portions and/or intermediate cover.

5.4.1.8 Blower Rotation Limitation

In one form of the present technology, the RPT device 8000 comprises a blower rotation limitation structure configured to minimise or at least reduce rotation of the blower 8030 during use. It will be appreciated that parts of the blower which rotate during normal use of the blower, for example the impellers 8033A, 8033B, 8033C, are not limited from rotating. Rotation of the blower 8030 may cause electrical connections to/from the blower to be stressed, which may result in disconnection of the electrical connections. For example, if blower 8030 shown in FIG. 4H rotates on its longitudinal axis, electrical connector 8090 will be pulled tight as it is physically connected to the housing 8031 of blower 8030, and may rip or be disconnected from PCBA 8070.

The form of the technology shown in FIGS. 4Z1 and 4Z2 addresses this problem. As best shown in FIG. 4Z1, blower 8030 comprises a collar 8036 provided around inlet 8032. Collar 8036 comprises one or more notches 8037 around its circumference. Notch 8037 may be any break, gap or recess in collar 8036. As best shown in FIG. 4Z2, second plate assembly 8060 comprises a structure configured to engage with notch 8037 to reduce rotation of the blower 8030. For example, inlet end suspension 8064 may comprise a tongue 8066 that protrudes radially inwardly from an inner edge of the circular aperture in inlet end suspension 8064 that aligns with inlet 8032 in the assembled RPT device 8000. Tongue 8066 is configured to engage with notch 8037 in collar 8036 in the assembled device and prevent or reduce rotation of the blower 8030 with respect to other parts of RPT device 8000. Notch 8037 is positioned at an orientation around collar 8036 so that the electrical connector 8090 is not under stress, for example by being stretched tightly, when RPT device 8000 is assembled. Notch 8037 may also be positioned to avoid electrical connector 8090 being overly slack when RPT device 8000 is assembled as this may lead to the electrical connector 8090 being tangled with other parts of the RPT device 8000 during use. It will be appreciated that the position of tongue 8066 and notch 8037 may differ from the position in which they are shown in FIGS. 4Z1 and 4Z2.

Other rotation limitation structures may be provided in other forms of the technology, for example other structures in which a first rotation limitation member provided on the blower suspension interacts with a second rotation limitation member provided on the blower. In one example, a tongue may be provided on collar 8036 that engages with a notch provided in inlet end suspension 8064. In another example, a notch or tongue structure may be provided at the outlet end of the blower that is configured to engage with a complementary notch or tongue structure in the first plate assembly 8050 in addition to or instead of the notch-and-tongue structure that is provided at the inlet end, such as has been described above. In other forms of the technology, other interacting structures between a part of the blower 8030 and one or both of first plate assembly 8050 and second plate assembly 8060 may be provided including, but not limited to, interlocks, clips and adhering parts.

In some forms of the technology, the RPT device 8000 may be structured and arranged so that the electrical connection between the blower 8030 and the PCBA 8070 is unlikely to be disconnected even if the blower 8030 does rotate. In one exemplary form of the technology, the electrical connector 8090 between the blower 8030 and the PCBA 8070, for example a longitudinal middle section of the electrical connector 8090, engages with another part of the RPT device 8000 in order to isolate two parts of the electrical connector 8090 from movement of the other part.

One example of such a structure is illustrated in FIGS. 4Z1 and 4Z2. In this example, electrical connector 8090 comprises one or more tabs 8092 located in a longitudinal middle section of the electrical connector 8090 (e.g. not at the ends of the electrical connector 8090), the tabs 8092 extending outwards from the electrical connector 8090 in a direction perpendicular to the direction in which conducting paths extend along the length of the electrical connector 8090. Tabs 8092 may be integral to the electrical connector 8090 and formed, for example, from a thin polymer film to which the conducting paths of the electrical connector are attached. Tabs 8092 may have one or more holes provided therein. Alternatively, the tabs may be in the form of hooks or other structures able to substantially fixedly engage the electrical connector 8090 to another part of the RPT device 8000. Alternatively still, the tabs or any other part of the electrical connector 8090 could be fastened to another part of the RPT device 8000 using another mechanism, for example adhesive.

As shown in FIG. 4Z2, the bottom housing portion 8014 comprises one or more connector anchors 8011 for anchoring the longitudinal middle section of the electrical connector 8090 to another part of the RPT device. Connector anchors 8011 may take the form of posts integrally formed as part of the bottom housing portion 8014 or the posts may be attached to a main body of the bottom housing portion 8014. The posts are sized and configured so that the posts can be inserted through the holes in tabs 8092 of the electrical connector. In the assembled RPT device 8000, the posts act to isolate the parts of electrical connector 8090 on either side of tabs 8092 from each other. That is, rotation of blower 8030 during use may result in a pulling force being transmitted through electrical connector 8090 onto tabs 8092 but, since this force is transmitted to posts, rotation of the blower will not cause electrical connector 8090 to be pulled out of connection with PCBA 8070. Similarly, vibrations of the blower 8030 transmitted through electrical connector 8090 are impeded by connector anchors 8011 and may help to reduce vibrations in other parts of the RPT device 8000.

5.4.1.9 Air Filter(s)

An RPT device in accordance with one form of the present technology may include an air filter, or a plurality of air filters.

In one form, an inlet air filter is located at the beginning of the pneumatic path upstream of the blower, such as housed in the cover plate 8021.

In one form, an outlet air filter, for example an antibacterial filter, is located between an outlet of the pneumatic block and a patient interface 3000.

5.4.1.10 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers may be located upstream and/or downstream of the blower. The one or more transducers may be constructed and arranged to measure properties such as a flow rate, a pressure or a temperature at that point in the pneumatic path.

In one form of the present technology, one or more transducers may be located proximate to the patient interface 3000.

In one form, a signal from a transducer may be filtered, such as by low-pass, high-pass or band-pass filtering.

5.4.1.10.1 Flow Rate Sensor

A flow rate sensor in accordance with the present technology may be based on a differential pressure transducer, for example, an SDP600 Series differential pressure transducer from SENSIRION.

In one form, a signal representing a flow rate such as a total flow rate Qt from the flow rate sensor may be received by a central controller.

5.4.1.10.2 Pressure Sensor

A pressure sensor in accordance with the present technology may be located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor may be received by the central controller.

5.4.1.10.3 Motor Speed Transducer

In one form of the present technology a motor speed transducer may be used to determine a rotational velocity of the motor and/or the blower. A motor speed signal from the motor speed transducer may be provided to a therapy device controller. The motor speed transducer may, for example, be a speed sensor, such as a Hall effect sensor.

5.4.1.11 Anti-Spill Back Valve

In one form of the present technology, an anti-spill back valve may be located between the humidifier 5000 and the pneumatic block. The anti-spill back valve is constructed and arranged to reduce the risk that water will flow upstream from the humidifier 5000, for example to the motor of the blower.

5.4.1.12 Air Circuit

An air circuit 4170 in accordance with an aspect of the present technology is a conduit or a tube constructed and arranged in use to allow a flow of air to travel between two components such as the pneumatic block and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in United States Patent Application No. US/2011/0023874, which is incorporated herewithin in its entirety by reference.

5.4.1.13 Oxygen Delivery

In one form of the present technology, supplemental oxygen may be delivered to one or more points in the pneumatic path, such as upstream of the pneumatic block, to the air circuit 4170 and/or to the patient interface 3000.

5.4.2 RPT Device Electrical Components 5.4.2.1 Power Supply

A power supply may be located internal or external of the external housing of the RPT device 8000.

In one form of the present technology, power supply provides electrical power to the RPT device 8000 only. In another form of the present technology, power supply provides electrical power to both RPT device 8000 and humidifier 5000.

5.4.2.2 Input Devices

In one form of the present technology, an RPT device 8000 includes one or more input devices in the form of buttons, switches or dials to allow a person to interact with the device, e.g., buttons 8003, 8004. The buttons, switches or dials may be physical devices, or software devices accessible via a touch screen. The buttons, switches or dials may, in one form, be physically connected to the external housing, or may, in another form, be in wireless communication with a receiver that is in electrical connection to the central controller.

In one form, the input device may be constructed and arranged to allow a person to select a value and/or a menu option.

5.4.2.3 Central Controller

In one form of the present technology, the central controller is one or a plurality of processors suitable to control an RPT device 8000, e.g., PCBA 8070 including main PCB 8072 and secondary PCB 8074.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers, one or more input devices, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device may include a clock that is connected to the central controller.

5.4.2.5 Therapy Device Controller

In one form of the present technology, the blower may be under the control of a therapy device controller. The therapy device controller may be a therapy control module that forms part of the algorithms executed by the central controller.

In one form of the present technology, therapy device controller is a dedicated motor control integrated circuit. For example, in one form a MC33035 brushless DC motor controller, manufactured by ONSEMI is used.

5.4.2.6 Protection Circuits

The one or more protection circuits in accordance with the present technology may comprise an electrical protection circuit, a temperature and/or pressure safety circuit.

5.4.2.7 Memory

In accordance with one form of the present technology the RPT device includes memory, e.g., non-volatile memory. In some forms, memory may include battery powered static RAM. In some forms, memory may include volatile RAM.

Memory may be located on the PCBA. Memory may be in the form of EEPROM, or NAND flash.

Additionally or alternatively, RPT device includes a removable form of memory, for example a memory card made in accordance with the Secure Digital (SD) standard.

In one form of the present technology, the memory acts as a non-transitory computer readable storage medium on which is stored computer program instructions expressing the one or more methodologies described herein, such as the one or more algorithms

5.4.2.8 Data Communication Systems

In one form of the present technology, a data communication interface is provided, and is connected to the central controller. Data communication interface may be connectable to a remote external communication network and/or a local external communication network. The remote external communication network may be connectable to a remote external device. The local external communication network may be connectable to a local external device.

In one form, data communication interface is part of the central controller. In another form, data communication interface is separate from the central controller, and may comprise an integrated circuit or a processor.

In one form, remote external communication network is the Internet. The data communication interface may use wired communication (e.g. via Ethernet, or optical fibre) or a wireless protocol (e.g. CDMA, GSM, LTE) to connect to the Internet.

In one form, local external communication network utilises one or more communication standards, such as Bluetooth, or a consumer infrared protocol.

In one form, remote external device is one or more computers, for example a cluster of networked computers. In one form, remote external device may be virtual computers, rather than physical computers. In either case, such a remote external device may be accessible to an appropriately authorised person such as a clinician.

The local external device may be a personal computer, mobile phone, tablet or remote control.

5.4.2.9 Output Devices Including Optional Display, Alarms

An output device in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver receives as an input the characters, symbols, or images intended for display on the display, and converts them to commands that cause the display to display those characters, symbols, or images.

5.4.2.9.2 Display

A display is configured to visually display characters, symbols, or images in response to commands received from the display driver. For example, the display may be an eight-segment display, in which case the display driver converts each character or symbol, such as the figure "0", to eight logical signals indicating whether the eight respective segments are to be activated to display a particular character or symbol.

5.4.3 RPT Device Accessories

5.4.3.1 External Battery

An external battery 9000 according to some forms of the present technology is shown in FIGS. 4W1 and 4W2.

The external battery 9000 may be engageable with the RPT device 8000, for example as shown in FIGS. 4X1 to 4Y2. The external battery 9000 may comprise a guiding member to facilitate alignment and connection with the RPT device 8000 (as well as disconnection). In one form, the external battery 9000 may comprise one or more guide slots 9050, each configured to receive a respective guide rail 8019 of the RPT device 8000. The guide slot 9050 may further comprise a latch 9060 releasable by a latch button 9065. The latch 9060 may be configured to engage with the recessed slot 8110 along the guide rail 8019 of the RPT device 8000 to retain the RPT device 8000 with respect to the external battery 9000.

In some forms, the external battery 9000 may comprise a facia 9100 as shown in FIG. 4W1, the facia being engageable with an end of the RPT device 8000 as shown in FIG. 4Y1.

The facia 9100 may comprise at least one of an air inlet 9018 and an air outlet 9020, for extending an air path of the RPT device 8000. The air inlet 9018 and/or the air outlet 9020 may be configured substantially identically to the housing inlet 8018 and the housing outlet 8020 respectively. Thus, a user may be able to use the same air conduit 4170 regardless of whether the air conduit is being connected to the RPT device 8000 or to the external battery 9000.

In some cases, the battery 9000 may comprise a muffler such that the noise output of the RPT device 8000 is reduced. For example, the muffler may reduce a noise output from the housing outlet 8020 so that it is reduced at the air outlet 9020. Additionally, or alternatively, the muffler may reduce a noise output from the housing inlet 8018 so that noise from (e.g., measured at) the air inlet 9018 is lower than noise from (e.g., measured at) the housing inlet 8018.

In some examples, the battery facia 9100 may comprise a muffling chamber located between the housing outlet 8020 and the air outlet 9020. In other examples, the battery facia 9100 may comprise a muffling chamber located between the housing inlet 8018 and the air inlet 9018. To this end, the air outlet 9020 may be displaced from the housing outlet 8020, e.g., by approximately 30 mm. It will be however understood that other means of noise reduction may be possible between the housing outlet 8020 and the air outlet 9020, and the housing inlet 8018 and the air inlet 9018.

The external battery may comprise one or more battery cells (e.g., Lithium-Ion cells, or Nickel-metal hydride cells) configured to store electrical energy, and a printed circuit board assembly (PCBA) connected thereto.

The PCBA may comprise components and/or circuitry for controlling one or more operations of the battery, such as power management, communication with the RPT device 8000 and/or voltage conversion.

The external battery may generate heat, such as from the PCBA and/or the battery cells. Thus, it may be preferred to manage heat output from the external battery such that the PCBA and the battery cells operate within their preferred environmental conditions.

In one aspect of the present technology, the external battery 9000 may be configured to be thermally coupled to the RPT device 8000. The RPT device 8000 comprises an air path within, wherein ambient air is drawn in through its inlet (e.g., housing inlet 8018) and delivered through its outlet (e.g., housing outlet 8020).

Thus, the air flow of the RPT device 8000 may be used to cool one or more components of the external battery 9000. That is, heat conducted from the external battery 9000 to the RPT device 8000 may be removed from the RPT device 8000 by convection.

The external battery 9000 may be configured such that its generated heat is more efficiently delivered to the RPT device 8000 for convective cooling. For example, higher heat generating components of the external battery 9000 may be located proximal to the RPT device 8000 when assembled. In another example, the external battery 9000 may comprise a thermally conductive element configured to deliver heat towards the RPT device 8000 when assembled.

In one form, such as shown in FIG. 4Y1 wherein the external battery 9000 is configured to couple below the RPT device, a higher heat generating component of the external battery 9000 may be located towards the top of the external battery to improve heat transfer. In another form, the external battery 9000 may comprise a heat pipe to improve thermal conduction from a higher heat generating component to an exterior of the external battery 9000, such that heat transfer to the RPT device 8000 may be improved when they are coupled together.

Furthermore, the external battery 9000 may be configured to improve thermal conductivity between it and the RPT device 8000. For example, the external battery 9000 may comprise one or more conductive portions (e.g., surfaces) configured to thermally couple with the RPT device 8000 for heat transfer when engaged thereto.

5.4.4 RPT Device Algorithms

5.4.4.1 Pre-Processing Module

As shown in FIG. 4V, a pre-processing module 4310 in accordance with one form of the present technology receives as an input a signal from a transducer, for example a flow rate sensor or pressure sensor, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.4.2 Therapy Control Module

Therapy control module 4330 in accordance with one aspect of the present technology receives as inputs the therapy parameters from the therapy parameter determination algorithm of the therapy engine module 4320, and controls the pressure generator to deliver a flow of air in accordance with the therapy parameters.

In one form of the present technology, the therapy parameter is a treatment pressure Pt, and the therapy control module 4330 controls the pressure generator to deliver a flow of air whose mask pressure Pm at the patient interface 3000 is equal to the treatment pressure Pt.

5.5 Humidifier

5.5.1 Humidifier Overview

The RPT device 8000 may be configured to be connected, in use, to a humidifier for changing the absolute humidity of air or gas for delivery to a patient relative to ambient air. In one form the humidifier is in the form of a moisture exchanger positioned in the path of air circuit 4170. Alternatively, RPT device 8000 may deliver air to a patient without humidification.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Mechanical Components

5.5.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.5.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.5.3 Humidifier Electrical & Thermal Components

The humidifier 5000 may comprise a number of electrical and/or thermal components such as those listed below.

5.5.3.1 Humidifier Transducer(s)

The humidifier 5000 may comprise one or more humidifier transducers (sensors) 5210 instead of, or in addition to, transducers described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller and/or the humidifier controller 5250. In some forms, a humidifier transducer may be located externally to the humidifier 5000 (such as in the air circuit 4170) while communicating the output signal to the controller.

5.5.3.1.1 Pressure Transducer

One or more pressure transducers 5212 may be provided to the humidifier 5000 in addition to, or instead of, a pressure sensor provided in the RPT device.

5.5.3.1.2 Flow Rate Transducer

One or more flow rate transducers 5214 may be provided to the humidifier 5000 in addition to, or instead of, a flow rate sensor provided in the RPT device.

5.5.3.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.5.3.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.5.3.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.5.3.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4170 and/or a heating element controller 5252 configured to control the temperature of a heating element 5240.

5.6 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate typically refers to an instantaneous quantity unless stated otherwise. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

Patient: A person, whether or not they are suffering from a respiratory disease.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.7.2 Terms for RPT Devices

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

5.7.3 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240

Polycarbonate: a typically transparent thermoplastic polymer of Bisphenol-A Carbonate.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| Number | Feature Item |
|---|---|
| inlet tube array | 52A |
| inlet tube array | 52B |
| inlet tube array | 52C |
| patient | 1000 |
| bed partner | 1100 |
| patient interface | 3000 |
| seal-forming structure | 3100 |
| plenum chamber | 3200 |
| stabilising structure | 3300 |
| vent | 3400 |
| connection port | 3600 |
| forehead support | 3700 |
| RPT device | 4000 |
| air circuit | 4170 |
| pre-processing module | 4310 |
| pressure compensation algorithm | 4312 |
| vent flow rate estimation algorithm | 4314 |
| leak flow rate estimation algorithm | 4316 |
| flow rate estimation algorithm | 4318 |
| therapy engine module | 4320 |
| therapy control module | 4330 |
| humidifier | 5000 |
| humidifier inlet | 5002 |
| humidifier outlet | 5004 |
| humidifier base | 5006 |

-continued

| Number | Feature Item |
|---|---|
| reservoir | 5110 |
| conductive portion | 5120 |
| humidifier reservoir dock | 5130 |
| locking lever | 5135 |
| water level indicator | 5150 |
| humidifier transducer | 5210 |
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| RPT device | 8000 |
| first chamber | 8001 |
| second chamber | 8002 |
| power button | 8003 |
| button portion | 8003A |
| button portion | 8003B |
| bluetooth connection button | 8004 |
| opening | 8004A |
| button portion | 8004B |
| interior chamber portion | 8006 |
| interior chamber portion | 8007 |
| housing | 8010 |
| connector anchors | 8011 |
| top housing portion | 8012 |
| base mold | 8012A |
| overmold | 8012B |
| bottom housing portion | 8014 |
| base mold | 8014A |
| overmold | 8014B |
| slot | 8015A |
| slot | 8015B |
| first end portion | 8016 |
| interior rib | 8017 |
| housing inlet | 8018 |
| rail | 8019 |
| housing outlet | 8020 |
| cover plate | 8021 |
| second end portion | 8022 |
| opening | 8023 |
| faceplate | 8024 |
| opening | 8025 |
| tube portion | 8026 |
| tube portion | 8027 |
| interior wall | 8028 |
| end wall | 8028A |
| end wall | 8028B |
| blower | 8030 |
| housing | 8031 |
| inlet | 8032 |
| impeller | 8033A |
| impeller | 8033B |
| impeller | 8033C |
| outlet | 8034 |
| motor | 8035 |
| collar | 8036 |
| notch | 8037 |
| electrical connector portion | 8038 |
| intermediate cover | 8040 |
| base mold | 8040A |
| overmold | 8040B |
| slot | 8042A |
| slot | 8042B |
| main wall | 8044 |
| first plate assembly | 8050 |
| base plate | 8051 |
| inlet tube array | 8052 |
| first end portion | 8052A |
| second end portion | 8052B |
| tube portion | 8053 |
| opening | 8053A |
| blower suspension | 8054 |
| first end portion | 8054A |

-continued

| Number | Feature Item |
|---|---|
| second end portion | 8054B |
| gusset portion | 8054C |
| inlet tube | 8055 |
| outlet bellow | 8056 |
| end portion | 8056A |
| bellows portion | 8056B |
| projections | 8056C |
| pressure port | 8058 |
| sealing lip | 8059 |
| second plate assembly | 8060 |
| base plate | 8061 |
| flow tube array | 8062 |
| opening | 8063 |
| blower suspension | 8064 |
| outer portion | 8064A |
| inner portion | 8064B |
| intermediate portion | 8064C |
| flow tube | 8065 |
| first end portion | 8065A |
| second end portion | 8065B |
| tongue | 8066 |
| sealing lip | 8069 |
| PCBA | 8070 |
| main PCB | 8072 |
| secondary PCB | 8074 |
| electrical socket | 8080 |
| electrical connector | 8090 |
| connector tab | 8092 |
| recessed slot | 8110 |
| external battery | 9000 |
| air inlet | 9018 |
| air outlet | 9020 |
| guide slot | 9050 |
| latch | 9060 |
| latch button | 9065 |
| facia | 9100 |

The invention claimed is:

1. Apparatus for generating a supply of air at positive pressure for the amelioration or treatment of a respiratory disorder, the apparatus comprising:
 a housing;
 a blower supported within the housing, the blower comprising a blower housing and being structured and configured to produce a flow of air at positive pressure;
 a printed circuit board assembly supported within the housing and configured to control the blower, the printed circuit board assembly arranged exterior and spaced apart from the blower housing of the blower;
 a flexible electrical connector structured and configured to electrically and physically connect the blower to the printed circuit board assembly, the flexible electrical connector including a first end physically and electrically connected to a connector portion of the blower housing and a second end physically and electrically connected to a connector portion of the printed circuit board assembly; and
 a blower rotation limitation structure configured to reduce rotation of the blower housing of the blower relative to the housing about a longitudinal axis of the blower during use to prevent disconnection of the flexible electrical connector from the connector portion of the blower housing and/or the connector portion of the printed circuit board assembly.

2. Apparatus according to claim 1, wherein the apparatus comprises a first blower suspension structured and configured to support a first end of the blower.

3. Apparatus according to claim 2, wherein the blower rotation limitation structure comprises a first rotation limitation member provided on the first blower suspension, the first rotation limitation member interacting in use with a second rotation limitation member provided on the blower to limit rotation of the blower.

4. Apparatus according to claim 3, wherein the second rotation limitation member comprises a notch on the blower and the first rotation limitation member comprises a tongue provided to the first blower suspension, the notch and tongue being configured to engage with each other to limit rotation of the blower.

5. Apparatus according to claim 4, wherein the blower comprises a collar around a blower inlet and the notch is provided in the collar.

6. Apparatus according to claim 4, wherein the first blower suspension comprises a circular aperture and the tongue protrudes radially inwardly from an inner edge of the circular aperture.

7. Apparatus according to claim 2, wherein the apparatus comprises a second blower suspension structured and configured to support a second end of the blower, the second end being at an opposite end of the blower to the first end.

8. Apparatus according to claim 7, wherein the apparatus comprises:
 a first plate assembly, wherein the first plate assembly comprises the first blower suspension and the first blower suspension supports the blower adjacent a blower outlet of the blower; and
 a second plate assembly, wherein the second plate assembly comprises the second blower suspension and the second blower suspension supports the blower adjacent a blower inlet of the blower.

9. Apparatus according to claim 8, wherein the apparatus comprises at least one chamber and the first plate assembly comprises a first base plate that defines at least in part a wall of the at least one chamber and the second plate assembly comprises a second base plate that defines at least in part a wall of the at least one chamber.

10. Apparatus according to claim 9, wherein the at least one chamber comprises an air flow path and the flexible electrical connector passes through the at least one chamber while not being positioned directly in the air flow path.

11. Apparatus according to claim 9, wherein the apparatus further comprises at least one inlet tube structured and configured to allow ambient air to enter a chamber, wherein the flexible electrical connector is arranged to pass around a periphery of the at least one inlet tube.

12. Apparatus according to claim 1, wherein the blower rotation limitation structure is configured such that the flexible electrical connector is not under stress during operation of the apparatus.

13. Apparatus according to claim 1, wherein the apparatus comprises one or more connector anchors for anchoring a longitudinal middle section of the flexible electrical connector to another part of the apparatus.

14. Apparatus according to claim 13, wherein the one or more connector anchors comprises one or more posts.

15. Apparatus according to claim 13, wherein the housing comprises the one or more connector anchors.

16. Apparatus according to claim 13, wherein the longitudinal middle section of the flexible electrical connector comprises one or more holes and/or hooks configured to engage with the one or more connector anchors.

17. Apparatus according to claim 16, wherein the longitudinal middle section of the flexible electrical connector comprises one or more tabs, wherein the one or more holes and/or hooks are provided in the one or more tabs.

18. Apparatus according to claim 1, wherein the flexible electrical connector comprises at least one of: a flexible circuit board; flexible printed circuit; and a flexible flat cable.

19. Apparatus according to claim 1, wherein the blower housing includes an air inlet and an air outlet, and the air inlet and the air outlet are coaxial with the longitudinal axis of the blower.

20. Apparatus for generating a supply of air at positive pressure for the amelioration or treatment of a respiratory disorder, the apparatus comprising:
  a housing;
  a blower supported within the housing, the blower comprising a blower housing and being structured and configured to produce a flow of air at positive pressure;
  a first blower suspension structured and configured to support a first end of the blower adjacent a blower outlet of the blower within the housing;
  a second blower suspension structured and configured to support a second end of the blower adjacent a blower inlet of the blower within the housing, the second end being at an opposite end of the blower to the first end; and
  a blower rotation limitation structure arranged at the first end of the blower and/or the second end of the blower, the blower rotation limitation structure configured to reduce rotation of the blower housing of the blower relative to the housing and the first and second blower suspensions about a longitudinal axis of the blower during use.

21. Apparatus according to claim 20, wherein the apparatus comprises a first plate assembly and a second plate assembly, wherein the first plate assembly comprises the first blower suspension and a first base plate and the second plate assembly comprises the second blower suspension and a second base plate.

22. Apparatus according to claim 21, wherein the apparatus comprises at least one chamber and the first base plate defines at least in part a wall of the at least one chamber and the second base plate defines at least in part a wall of the at least one chamber.

23. Apparatus for generating a supply of air at positive pressure for the amelioration or treatment of a respiratory disorder, the apparatus comprising:
  a housing;
  a blower supported within the housing, the blower being structured and configured to produce a flow of air at positive pressure;
  a printed circuit board assembly supported within the housing and configured to control the blower, the printed circuit board assembly arranged exterior and spaced apart from the blower;
  a flexible electrical connector structured and configured to electrically and physically connect the blower to the printed circuit board assembly, the flexible electrical connector including a first end physically and electrically connected to a connector portion of the blower and a second end physically and electrically connected to a connector portion of the printed circuit board assembly, and the flexible electrical connector including a longitudinal middle section between the first end and the second end; and
  one or more connector anchors structured and arranged to anchor the longitudinal middle section of the flexible electrical connector to another part of the apparatus to prevent disconnection of the flexible electrical connector from the connector portion of the blower and/or the connector portion of the printed circuit board assembly.

24. Apparatus according to claim 23, wherein the one or more connector anchors comprises one or more posts.

25. Apparatus according to claim 23, wherein the housing comprises the one or more connector anchors.

26. Apparatus according to claim 23, wherein the longitudinal middle section of the flexible electrical connector comprises one or more holes and/or hooks configured to engage with the one or more connector anchors.

27. Apparatus according to claim 26, wherein the longitudinal middle section of the flexible electrical connector comprises one or more tabs, wherein the one or more holes and/or hooks are provided in the one or more tabs.

28. Apparatus according to claim 23, wherein the flexible electrical connector comprises at least one of: a flexible circuit board; flexible printed circuit; and a flexible flat cable.

29. Apparatus according to claim 23, further comprising a blower rotation limitation structure configured to reduce rotation of the blower during use.

30. Apparatus for generating a supply of air at positive pressure for the amelioration or treatment of a respiratory disorder, the apparatus comprising:
  a housing;
  a blower supported within the housing, the blower being structured and configured to produce a flow of air at positive pressure; and
  a blower suspension mounted to the housing and structured and arranged to support the blower in the housing, wherein the blower suspension comprises a flexible, elastomeric material, and
  wherein the flexible, elastomeric material of the blower suspension is under tension when the blower suspension is mounted to the housing to suspend the blower within the housing and isolate vibrations in the blower.

31. Apparatus according to claim 30, wherein the apparatus comprises a first plate assembly, the first plate assembly comprising the blower suspension.

32. Apparatus according to claim 31, wherein the apparatus comprises a second plate assembly to support the blower.

33. Apparatus according to claim 32, wherein the housing comprises a first interior slot structured and configured to support the first plate assembly and a second interior slot structured and configured to support the second plate assembly.

34. Apparatus according to claim 33, wherein, when the first and second plate assemblies are not mounted in the first and second interior slots, the first and second plate assemblies are separated by a first distance and, when the first and second plate assemblies are mounted in the first and second interior slots, the first and second plate assemblies are separated by a second distance, the first distance being less than the second distance.

35. Apparatus according to claim 34, wherein the blower suspension is a first blower suspension and the second plate assembly comprises a second blower suspension.

36. Apparatus according to claim 35, wherein the second blower suspension supports an inlet or an outlet end of the blower.

37. Apparatus according to claim 30, wherein the blower suspension supports an inlet or an outlet end of the blower.

* * * * *